United States Patent
Gryska et al.

(10) Patent No.: US 9,658,198 B2
(45) Date of Patent: May 23, 2017

(54) METHOD FOR IDENTIFICATION AND QUANTITATIVE DETERMINATION OF AN UNKNOWN ORGANIC COMPOUND IN A GASEOUS MEDIUM

(71) Applicant: 3M INNOVATIVE PROPERTIES COMPANY, St. Paul, MN (US)

(72) Inventors: Stefan H. Gryska, Woodbury, MN (US); Michael C. Palazzotto, Woodbury, MN (US); Derek M. Maanum, St. Paul, MN (US); Myungchan Kang, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 582 days.

(21) Appl. No.: 14/356,772

(22) PCT Filed: Dec. 10, 2012

(86) PCT No.: PCT/US2012/068748
§ 371 (c)(1),
(2) Date: May 7, 2014

(87) PCT Pub. No.: WO2013/090188
PCT Pub. Date: Jun. 20, 2013

(65) Prior Publication Data
US 2014/0309947 A1    Oct. 16, 2014

Related U.S. Application Data

(60) Provisional application No. 61/569,987, filed on Dec. 13, 2011.

(51) Int. Cl.
*G01N 7/00* (2006.01)
*G01N 33/00* (2006.01)
(Continued)

(52) U.S. Cl.
CPC ....... *G01N 33/0047* (2013.01); *G01N 21/783* (2013.01); *G01N 27/227* (2013.01); *G01N 33/0018* (2013.01); *G01N 33/0031* (2013.01)

(58) Field of Classification Search
CPC .................................................. G01N 33/0047
(Continued)

(56) References Cited

U.S. PATENT DOCUMENTS

| 4,638,443 A | 1/1987 | Kaneyasu |
| 5,569,838 A | 10/1996 | Broedel |

(Continued)

FOREIGN PATENT DOCUMENTS

| CN | 101685077 | 3/2010 |
| JP | 6-281610 | 10/1994 |

(Continued)

OTHER PUBLICATIONS

Budd, "Free volume and intrinsic microporosity in polymers", Journal of Materials Chemistry, Jan. 2005, vol. 15, pp. 1977-1986.

(Continued)

*Primary Examiner* — Robert Huber
*Assistant Examiner* — Tarun Sinha
(74) *Attorney, Agent, or Firm* — Bradford B. Wright; Yufeng Dong

(57) ABSTRACT

A method for identifying and quantitatively analyzing an unknown organic compound in a gaseous medium. More specifically, the method provides a gas sensor array (120a, 120b, 120c, 120d) coupled to a diluting channeling gas inlet (105) with a honeycomb configuration. Each sensor (120a, 120b, 120c, 120d) in the array receives the test gas after successive dilutions. Detected gas are identified by correlating the responses of each sensor with its associated dilution.

11 Claims, 6 Drawing Sheets

(51) Int. Cl.
   *G01N 27/22* (2006.01)
   *G01N 21/78* (2006.01)

(58) Field of Classification Search
   USPC ............... 73/31.02, 335.05, 334.05; 436/149
   See application file for complete search history.

(56) References Cited

U.S. PATENT DOCUMENTS

| | | | |
|---|---|---|---|
| 5,709,792 | A | 1/1998 | Zdanevitch |
| 6,165,347 | A | 12/2000 | Warburton |
| 6,320,388 | B1 | 11/2001 | Sun |
| 6,338,266 | B1 | 1/2002 | Warburton |
| 6,435,003 | B1 | 8/2002 | Warburton |
| 6,455,319 | B1 | 9/2002 | Lewis |
| 6,571,603 | B1 | 6/2003 | Doleman |
| 6,640,626 | B2 | 11/2003 | Saikalis |
| 6,691,582 | B1 | 2/2004 | Nawa |
| 6,815,211 | B1 | 11/2004 | Blazewicz |
| 6,895,338 | B2 | 5/2005 | Hsiung |
| 7,160,690 | B2 | 1/2007 | Orser |
| 7,200,495 | B2 | 4/2007 | Desai |
| 7,323,343 | B2 | 1/2008 | Cox |
| 7,449,146 | B2 | 11/2008 | Rakow |
| 7,556,774 | B2 | 7/2009 | Rakow |
| 7,680,607 | B1 | 3/2010 | Smulko |
| 7,767,143 | B2 | 8/2010 | Wendland |
| 7,906,233 | B2 | 3/2011 | Wang |
| 8,564,740 | B2 | 10/2013 | Schultz |
| 2002/0098119 | A1 | 7/2002 | Goodman |
| 2003/0166296 | A1 | 9/2003 | Morrison |
| 2003/0235817 | A1 | 12/2003 | Bartkowiak |
| 2005/0014179 | A1 | 1/2005 | Karlsson |
| 2005/0045493 | A1 | 3/2005 | Mahurin |
| 2005/0148003 | A1 | 7/2005 | Keith |
| 2006/0078960 | A1 | 4/2006 | Hunter |
| 2006/0099715 | A1 | 5/2006 | Munoz et al. |
| 2006/0246273 | A1 | 11/2006 | McKeown |
| 2006/0249402 | A1 | 11/2006 | Snow |
| 2007/0060811 | A1 | 3/2007 | Roberts |
| 2007/0118027 | A1 | 5/2007 | Baker |
| 2007/0177130 | A1 | 8/2007 | MacIntyre |
| 2007/0190637 | A1 | 8/2007 | Samsoondar |
| 2007/0299617 | A1 | 12/2007 | Willis |
| 2008/0086273 | A1 | 4/2008 | Shults |
| 2008/0137066 | A1 | 6/2008 | Weinstein |
| 2008/0161666 | A1 | 7/2008 | Feldman |
| 2008/0270039 | A1 | 10/2008 | Dunn |
| 2008/0288182 | A1 | 11/2008 | Cline |
| 2008/0312859 | A1 | 12/2008 | Skyggebjerg |
| 2009/0018426 | A1 | 1/2009 | Markle |
| 2009/0076360 | A1 | 3/2009 | Brister |
| 2009/0112478 | A1 | 4/2009 | Mueller |
| 2009/0192745 | A1 | 7/2009 | Kamath |
| 2010/0079130 | A1 | 4/2010 | Hong et al. |
| 2010/0189600 | A1 | 7/2010 | Hulteen |
| 2010/0277740 | A1 | 11/2010 | Hulteen |
| 2010/0325073 | A1 | 12/2010 | Haick |
| 2011/0045601 | A1* | 2/2011 | Gryska ............... G01N 27/221 436/149 |
| 2013/0088244 | A1 | 4/2013 | Gryska |
| 2013/0186177 | A1 | 7/2013 | Palazzotto |
| 2013/0229194 | A1 | 9/2013 | Palazzotto |
| 2014/0021967 | A1 | 1/2014 | Kang |
| 2014/0025326 | A1 | 1/2014 | Kang |
| 2014/0028333 | A1 | 1/2014 | Palazzotto |
| 2014/0076048 | A1 | 3/2014 | Gryska |
| 2014/0111809 | A1 | 4/2014 | Kang |

FOREIGN PATENT DOCUMENTS

| | | |
|---|---|---|
| JP | 2005-528629 A | 9/2005 |
| JP | 2010-540966 A | 12/2010 |
| JP | 2012-522249 A | 9/2012 |
| JP | 2014-514562 A | 6/2014 |
| WO | WO 99-08105 | 2/1999 |
| WO | WO 99-29230 | 6/1999 |
| WO | WO 00-79268 | 12/2000 |
| WO | WO 01-01121 | 1/2001 |
| WO | WO 01-81890 | 11/2001 |
| WO | WO 03-029800 | 4/2003 |
| WO | WO 03-063699 | 7/2003 |
| WO | WO 2005-012397 | 2/2005 |
| WO | WO 2007-029033 | 3/2007 |
| WO | WO 2008-077745 | 7/2008 |
| WO | WO 2009-053981 | 4/2009 |
| WO | WO 2009-045733 | 9/2009 |
| WO | WO 2009-046011 | 9/2009 |
| WO | WO 2010-075333 | 7/2010 |
| WO | WO 2010-117599 | 10/2010 |
| WO | WO 2011-159480 | 12/2011 |
| WO | WO 2012-044419 | 4/2012 |
| WO | WO 2012-050686 | 4/2012 |
| WO | WO 2012-141883 | 10/2012 |
| WO | WO 2012-141894 | 10/2012 |
| WO | WO 2012-141925 | 10/2012 |
| WO | WO 2012-141958 | 10/2012 |
| WO | WO 2012-170248 | 12/2012 |
| WO | WO 2012-174099 | 12/2012 |

OTHER PUBLICATIONS

Budd, "Polymers of intrinsic microporosity (PIMs): robust, solution-processable, organic nanoporous materials", Chemical Communications, 2004, vol. 2, pp. 230-231.

Budd, "Solution-processed, Organophilic Membrane Derived from a polymer of Intrinsic Microporosity", Advanced Materials, Mar. 2004, vol. 16, No. 5, pp. 456-459.

Carta, "Novel Spirobisindanes for Use as Precursors to Polymers of Intrinsic Microporosity", Organic Letters, 2008, vol. 10, No. 13, pp. 2641-2643.

Dai, "A capacitive humidity sensor integrated with micro heater and ring oscillator circuit fabricated by CMOS-MEMS technique", Sensors and Actuators B, 2007, vol. 122, pp. 375-380.

Endres, "A gas sensor system with dielectric and mass sensors", Sensors and Actuators B, 1992, vol. 6, pp. 285-288.

Ghanem, "High-Performance Membranes from Polyimides with Intrinsic Microporosity", Advanced Materials, 2008, vol. 20, pp. 2766-2771.

Ghanem, "Polymers of Intrinsic Microporosity Derived from Bis(phenazyl) Monomers", Macromolecules, 2008, vol. 41, No. 5, pp. 1640-1646.

Iwaki, "Identification of Different Vapors Using a Single Temperature Modulated Polymer Sensor With a Novel Signal Processing Technique", IEEE Sensors Journal, Apr. 2009, vol. 9, No. 4, pp. 314-328.

Matsuguchi, "Capacitive-Type Humidity Sensors Using Polymerized Vinyl Carboxylate", Journal of Electrochem. Society, Mar. 1994, vol. 141, No. 3, pp. 614-618.

McKeown, "Polymers of Intrinsic Microporosity (PIMs): Bridging the Void between Microporous and Polymeric Materials", Chemistry, A European Journal, 2005, vol. 11, pp. 2610-2620.

Smiths Detection, The Cyranose 320 ENose User's Manual, Ed. 5, Rev. E, 2004, 102 pages.

International Search Report for PCT International Application No. PCT/US2012/068748 mailed on Feb. 11, 2013, 5 pages.

* cited by examiner

METHOD FOR IDENTIFICATION AND QUANTITATIVE DETERMINATION OF AN UNKNOWN ORGANIC COMPOUND IN A GASEOUS MEDIUM

FIELD

The present disclosure broadly relates to methods of identifying and quantifying an unknown organic compound in a gaseous medium.

BACKGROUND

Detection of volatile organic compounds (VOCs) in various environments is of concern in many applications. Examples of such environments include residential, commercial, and especially manufacturing locations wherein an airborne organic compound may be present. While various methods for analyzing such organic compounds have been devised, the currently available techniques (e.g., mass spectroscopy) that are capable of both identifying and quantifying the amount of a low level airborne organic compound are generally expensive, are typically bulky, and may need frequent calibration and maintenance.

SUMMARY

In one aspect, the present disclosure provides a method of detecting an unknown organic compound in a first gaseous medium, the method comprising:

providing a first sensor element comprising a first outer layer, a second outer layer, and a detection layer comprising a microporous material disposed between the first outer layer and the second outer layer, wherein at least one of the first outer layer or the second outer layer is permeable by the unknown organic compound, wherein the unknown organic compound has an unknown chemical identity, wherein the first sensor element has a first baseline response ($R^1_o$) with respect to a physical parameter in a second gaseous medium at a fixed temperature ($T_o$), and wherein the second gaseous medium is substantially equivalent to the first gaseous medium;

providing a second sensor element, substantially identical to the first sensor element, wherein the second sensor element has a second baseline response ($R^2_o$) with respect to the physical parameter in the presence of the unknown organic compound in a third gaseous medium at $T_o$, wherein the third gaseous medium is substantially equivalent to the first gaseous medium;

providing a reference library comprising a plurality of reference normalized response correlations, wherein each reference normalized response correlation corresponds to a different known reference organic compound having a respective different chemical identity, wherein each reference normalized response correlation is determined using a respective reference sensor element that is substantially identical to the first sensor element, wherein each reference normalized response correlation correlates a respective variable concentration ($C^{ref}_{var}$) of a respective known reference organic compound with a respective quantity $$(R^{ref}_{var} - R^{ref}_o)/R^{ref}_o$$

wherein $R^{ref}_{var}$ is a response of the respective reference sensor element with respect to the physical parameter at the respective variable concentration $C^{ref}_{var}$ of the respective known reference organic compound in a respective fourth gaseous medium at $T_o$, wherein the fourth gaseous medium is substantially equivalent to the first gaseous medium, and wherein $R^{ref}_o$ for each respective reference sensor element corresponds to a baseline response in the fourth gaseous medium at $T_o$;

obtaining an ambient sample containing the first gaseous medium and the unknown organic compound, wherein the unknown organic compound is present in an ambient concentration ($C_{amb}$) in the ambient sample;

preparing a first analytic sample from the ambient sample, wherein the first analytic sample includes a first concentration ($C_1$) of the unknown organic compound in a fifth gaseous medium that is substantially equivalent to the first gaseous medium, wherein $C_1$ is known relative to $C_{amb}$;

preparing a second analytic sample from the ambient sample, wherein the second analytic sample includes a second concentration ($C_2$) of the unknown organic compound in a sixth gaseous medium that is substantially equivalent to the first gaseous medium, wherein $C_2$ is known relative to $C_{amb}$, wherein $C_1$ and $C_2$ are different, and wherein neither $C_1$ nor $C_2$ is zero;

exposing the first sensor element to the first analytic sample, measuring a first response ($R^1$) of the first sensor element with respect to the physical parameter at $T_o$, and obtaining a first normalized response $$R^1_{norm} = (R^1 - R^1_o)/R^1_o;$$

exposing the second sensor element to the second analytic sample, measuring a second response ($R^2$) of the second sensor element with respect to a physical parameter at $T_o$, and obtaining a second normalized response $$R^2_{norm} = (R^2 - R^2_o)/R^2_o;\text{ and}$$

comparing a data set comprising $R^1_{norm}$ at $C_1$ and $R^2_{norm}$ at $C_2$ to the plurality of reference normalized response correlations in the reference library;

selecting a matched normalized response correlation that best matches the data set from among the plurality of reference normalized response correlations in the reference library; and assigning the chemical identity of the known reference organic compound corresponding to the matched normalized response correlation to the unknown organic compound; and determining $C_{amb}$, by determining a reference concentration $C^{ref}_m$ associated with a normalized response value equal to $R^1_{norm}$ of the matched normalized response correlation, and then multiplying $C^{ref}_m$ by a known factor equal to $C_{amb}/C_1$.

In some embodiments, the first outer layer is disposed on a substrate. In some embodiments, the first gaseous medium comprises air. In some embodiments, the first outer layer and the second outer layer are conductive, the detection layer is dielectric, and the physical parameter comprises capacitance of the first sensor element. In some embodiments, wherein the first outer layer is semi-reflective, the second outer layer is at least partially reflective, the detection layer is optically transmissive, and the physical parameter comprises a wavelength shift of reflected light that is incident on the first outer layer. In some embodiments, $T_o$ is in a range of from 40° C. to 80° C. In some embodiments, the microporous material comprises an organic polymer of intrinsic microporosity. In some embodiments, the organic polymer of intrinsic microporosity comprises macromolecules comprising generally planar groups connected by rigid linkers, the rigid linkers having a point of contortion such that the generally planar groups adjacent to each of the rigid linkers are held in a non-coplanar orientation. In some embodiments, $C_{amb}$ and $C_1$ are the same.

In some embodiments, the method further comprises:

preparing a third analytic sample from the ambient sample, wherein the third analytic sample includes a third concentration ($C_3$) of the unknown organic compound in a seventh gaseous medium that is substantially equivalent to the first gaseous medium, wherein $C_3$ is known relative to $C_{amb}$, wherein the data set further comprises $R^3{}_{norm}$ at concentration $C_3$ of the unknown organic compound in the third analytic sample, wherein $R^3{}_{norm}$ is obtained by exposing a third sensor element to the third analytic sample, measuring a third response ($R^3$) of the third sensor element to the third analytic sample with respect to the physical parameter at $T_o$, and obtaining a third normalized response $R^3{}_{norm} = (R^3 - R^3{}_o)/R^3{}_o$, wherein the third sensor element is substantially identical to the first sensor element, wherein the third sensor element has a third baseline response ($R^3{}_o$) with respect to the physical parameter in the seventh gaseous medium at $T_o$, wherein $C_3$ is different than $C_1$ and $C_2$, and wherein $C_3$ is not zero.

Advantageously, using relatively simple and inexpensive sensing equipment (e.g., as compared to a mass spectrometer), methods according to the present disclosure can readily identify (e.g., from a single sample) both the identity and concentration of an unknown organic compound (from among a set of known reference organic compounds) in a gaseous medium such as, for example, ambient air in a workplace environment wherein organic compounds associated with utilized processes and/or materials may be present.

As used herein:

the term "baseline response" refers to the response of a sensor element in the gaseous medium in the absence of any organic compound;

the term "organic polymer" refers to a polymer comprising carbon atoms that are bonded to carbon and hydrogen atoms, and may contain additional atoms (e.g., N, S, O);

The features and advantages of the present disclosure will be further understood upon consideration of the detailed description as well as the appended claims.

While the above-identified drawing figures set forth several embodiments of the present disclosure, other embodiments are also contemplated, for example, as noted in the discussion. In all cases, the disclosure is presented by way of representation and not limitation. It should be understood that numerous other modifications and embodiments can be devised by those skilled in the art, which fall within the scope and spirit of the principles of the disclosure. The figures may not be drawn to scale. Like reference numbers may have been used throughout the figures to denote like parts.

DETAILED DESCRIPTION

In general, methods according to the present disclosure are generally effective for organic compounds that have sufficient vapor pressure to be present at detectable levels in the ambient sample. In some cases, the organic compound may be present as an aerosol. Exemplary organic compounds that may be used in practicing the present disclosure (e.g., as an unknown organic compound or a known reference organic compound) include aliphatic hydrocarbons (e.g., propane, butane, hexane, propylene, octane, d-limonene, cyclohexene, and cyclohexane), aromatic hydrocarbons (benzene, toluene, styrene, xylene, chlorobenzene, and naphthalene), fluorinated organic compounds (e.g., hydrofluorocarbons, hydrofluoroethers, and chlorofluorocarbons), ketones (e.g., acetone and methyl ethyl ketone), nitriles (e.g., acetonitrile and benzonitrile), halogenated aliphatic hydrocarbons (e.g., chloromethane, chloroform, dichloroethane, methylene chloride, 1,1,1-trichloroethane, carbon tetrachloride, dichloroethylene, and tetrachloroethylene), esters (e.g., vinyl acetate, ethyl acetate, butyl acetate, and methyl benzoate), sulfur-containing organic compounds (e.g., phenyl mercaptan and dimethyl sulfide), ethers (e.g., methyl isobutyl ether and diethyl ether, aldehydes (e.g., formaldehyde, benzaldehyde, hexanal, and acetaldehyde), alcohols (e.g., methanol, butanol, propanol, ethylene glycol monomethyl ether, 2-ethoxyethanol, and ethanol), amines (e.g., 2-aminopyridine), organic acids (e.g., acetic acid, propanoic acid), cyanates, isocyanates (e.g., methyl isocyanate and toluene-2,4-diisocyanate), and nitro-substituted organics (e.g., nitromethane and nitrobenzene).

Figure 1:
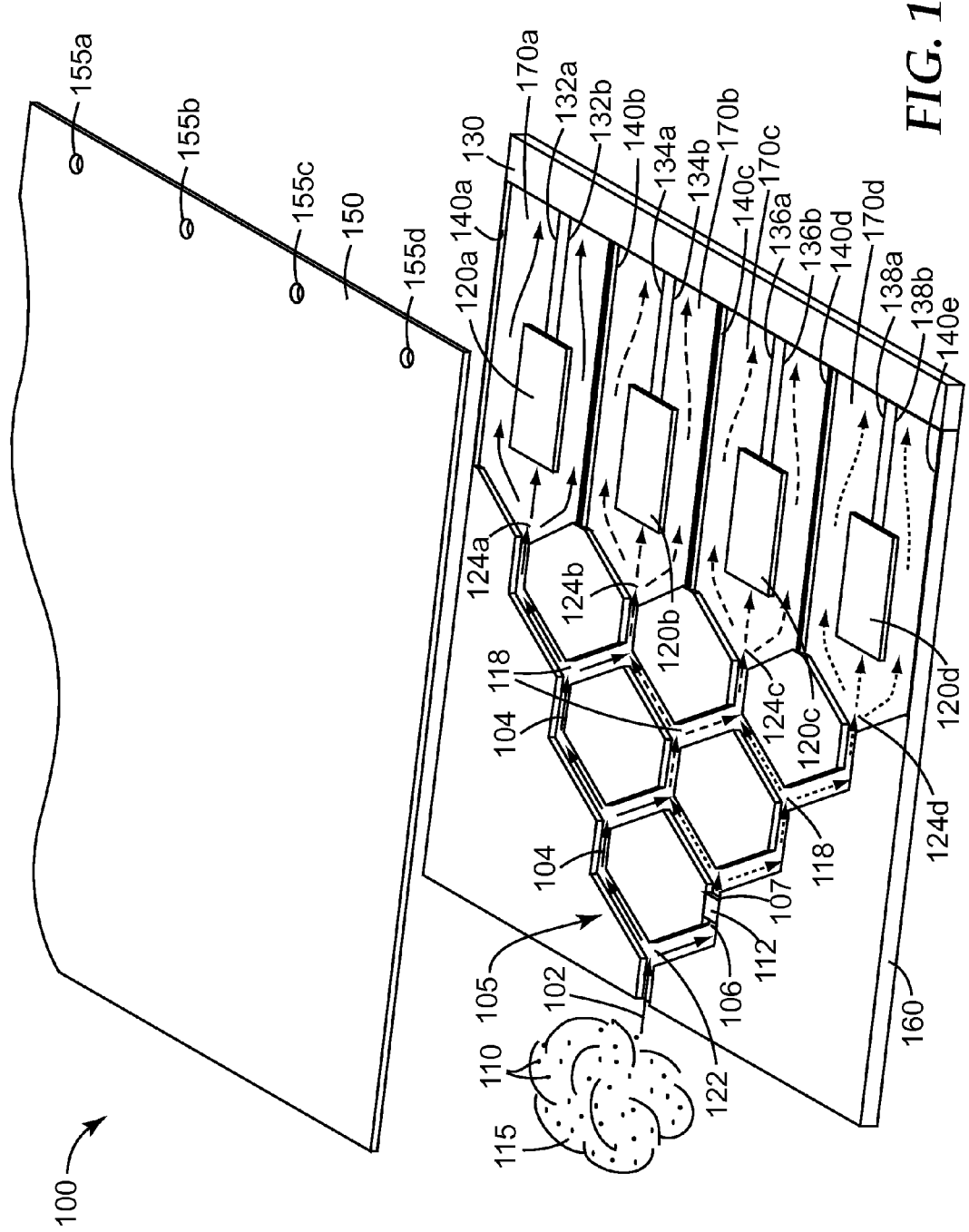
FIG. 1 is an exploded cutaway schematic perspective view of an exemplary apparatus 100 suitable for practice of one embodiment of the present disclosure.
Figure 2A:
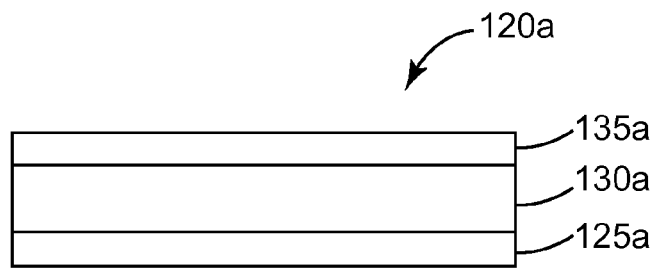
FIGS. 2A-2D are schematic side views of respective sensor elements 120a, 120b, 120c, 120d in FIG. 1.
Figure 2B:
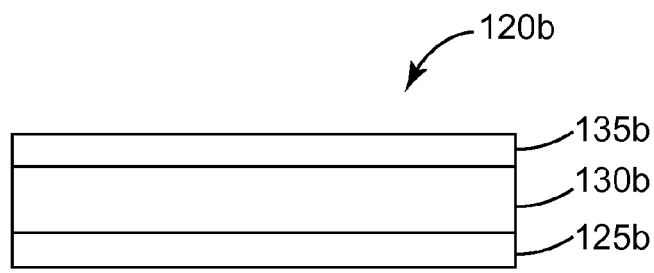
Figure 2C:
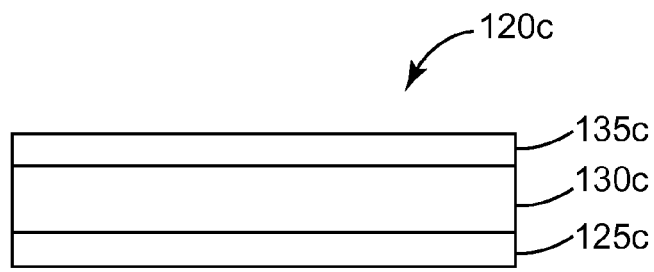
Figure 2D:
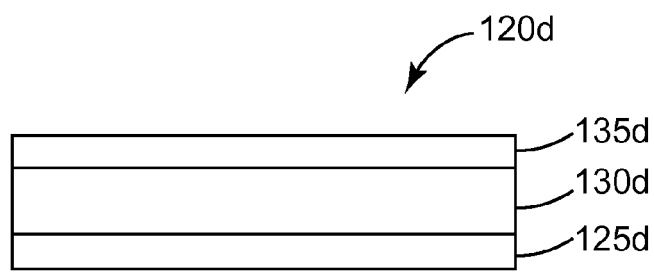

Referring now to FIG. 1, exemplary capacitance sensor device 100 suitable for practicing the present disclosure includes dispenser channels 105 having an inlet opening 122 and a plurality of outlet openings 124a, 124b, 124c, 124d which are independently in fluid communication with respective sensor elements 120a, 120b, 120c, 120d. Sensor elements 120a, 120b, 120c, 120d are disposed within respective isolated sensor chambers 170a, 170b, 170c, 170d formed by walls 140a, 140b, 140c, 140d, 140e, base 160, and cover 150, such that they function independently.

The base and cover can comprise any solid material that is impermeable by the organic compound and gaseous media used, and does not interfere with the electrical behavior of the sensor elements. Examples of useful materials include glass and plastic. Referring now to FIGS. 2A-2D, sensor elements 120a, 120b, 120c, 120d comprise respective first outer layers 125a, 125b, 125c, 125d, second outer layers 135a, 135b, 135c, 135d, and detection layers 130a, 130b, 130c, 130d disposed between them, respectively.

The detection layers may comprise, or even consist essentially of (i.e., contain only components that do not materially affect the absorption characteristics of), a microporous material. At least one of each of the corresponding first outer layers or second outer layers should be permeable by the unknown organic compound, thereby allowing it to diffuse readily into the detection layer where it may result in a change of a physical parameter (e.g., capacitance or reflectance spectrum peak shift) of the sensor element.

Examples of materials that can be used to make the first outer layer and/or second outer layer include, but are not limited to, organic materials, inorganic materials (e.g., metal oxides), metals, alloys, and mixtures and composites comprising any or all of these materials. Vapor-coated (e.g., thermal-vapor-coated, or sputter-coated) metals or metal oxides, or combinations thereof, may be used.

In embodiments wherein the sensor elements (e.g., first, second, third, and reference sensor elements) function to measure capacitance or an equivalent electrical property, the first and second outer layers should be sufficiently electrically conductive that they can function as electrodes. In such embodiments, the first and second outer layers preferably have a sheet resistance of less than about $10^7$ ohms/square. Exemplary electrically conductive materials include aluminum, nickel, titanium, tin, indium-tin oxide, gold, silver, platinum, palladium, carbon (including carbon nanotubes), copper, chromium, and combinations thereof. The first and second outer layers, and methods for their fabrication, are discussed in greater detail later in the specification.

The detection layers comprise microporous material. In this context, the terms "microporous" and "microporosity" mean that the material has a significant amount of internal, interconnected pore volume, with the mean pore size (as characterized, for example, by sorption isotherm techniques) being less than 100 nm, typically less than 10 nm. Such microporosity provides that molecules of organic analyte (if present) will be able to penetrate the internal pore volume of the material and take up residence in the internal pores. The presence of such analyte in the internal pores can alter physical properties of the material such as, for example, a change in the dielectric constant and/or refractive index.

Examples of suitable microporous materials that may be dielectric and/or optically transmissive include microporous silica and organic Polymers of Intrinsic Microporosity (PIMs). PIMs are polymeric materials with nanometer-scale pores due to inefficient crystal packing. Typically, PIMS are macromolecules comprising generally planar groups connected by rigid linkers, the rigid linkers having a point of contortion such that the generally planar groups adjacent to each of the rigid linkers are held in a non-coplanar orientation.

For example, in *Chemical Communications*, 2004, (2), pp. 230-231, Budd et al. report a series of PIMs containing dibenzodioxane linkages between rigid and/or contorted monomeric building blocks. Representative members of this family of polymers include those generated by condensation of Component A (e.g., A1, A2, or A3) with Component B (e.g., B1, B2, or B3) as shown in Table 1 according to Scheme 1 (below, wherein n is a positive integer).

SCHEME 1

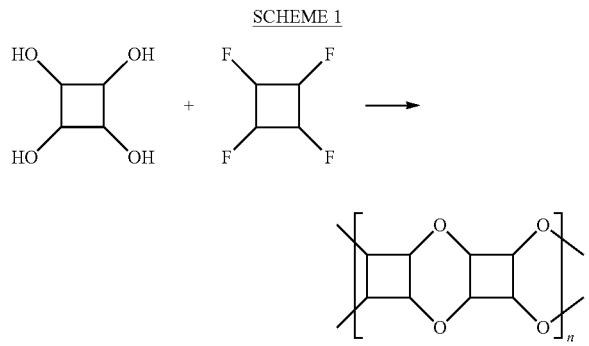

TABLE 1

| COMPONENT A | COMPONENT B |
|---|---|
| A1 | B1 |
| A2 | B2 |
| A3 | B3 |

Further suitable Components A and B, and resultant PIMs, are known in the art, for example, as reported by Budd et al. in *Journal of Materials Chemistry*, 2005, Vol. 15, pp. 1977-1986; by McKeown et al. in *Chemistry, A European Journal*, 2005, Vol. 11, pp. 2610-2620; by Ghanem et al. in *Macromolecules*, 2008, vol. 41, pp. 1640-1646; by Ghanem et al. in *Advanced Materials*, 2008, vol. 20, pp. 2766-2771; by Carta et al. in *Organic Letters*, 2008, vol. 10(13), pp. 2641-2643; in PCT Published Application WO 2005/012397 A2 (McKeown et al.); and in U.S. Patent Appl. Publ. No. 2006/0246273 (McKeown et al.), the disclosure of which is incorporated herein by reference.

Such polymers can be synthesized, for example, by a step-growth polymerization where a bis-catechol such as, e.g., A1 (5,5',6,6'-tetrahydroxy-3,3,3',3'-tetramethyl-1,1'-spirobisindane) is allowed to react with a fluorinated arene such as, e.g., B1 (tetrafluoroterephthalonitrile) under basic conditions. Due to the rigidity and contorted nature of the backbone of the resulting polymers, these polymers are unable to pack tightly in the solid state, and thus have at least 10 percent free volume and are intrinsically microporous.

PIMs may be blended with other materials. For example, a PIM may be blended with a material that itself is not an absorptive microporous material. Even though not contributing to an analyte response, such a material may be useful for other reasons. For example, such a material may allow the formation of a PIM-containing layer which has superior mechanical properties and the like. In some embodiments, PIMs may be dissolved in a common solvent with the other material to form a homogeneous solution, which may be cast to form an absorptive dielectric blend layer comprising both the PIM and the other polymer(s). PIM(s) may also be blended with a material that is an absorptive dielectric material (for example, zeolites, activated carbon, silica gel, hyper-crosslinked polymer networks and the like). Such materials may comprise insoluble materials that are suspended in a solution comprising of a PIM material. Coating and drying of such a solution/suspension may provide a composite detection layer comprising both the PIM material and the additional absorptive dielectric material.

PIMs are typically soluble in organic solvents such as, for example, tetrahydrofuran and can thus be cast as films from solution (e.g., by spin-coating, dip coating, or bar coating). However, characteristics (accessible thicknesses, optical clarity, and/or appearance) of films made from solutions of these polymers may vary markedly depending on the solvent or solvent system used to cast the film. For example, PIMs of higher molecular weights may need to be cast from relatively unusual solvents (e.g., cyclohexene oxide, chlorobenzene, or tetrahydropyran) to generate films with desirable properties for use in sensor elements as described herein. In addition to solution coating methods, the detection layer may be applied to the first outer layer by any other suitable method.

After a PIM is deposited (e.g., coated) or otherwise formed, for example, on the first outer layer so as to form a detection layer, it may be crosslinked using a suitable crosslinking agent such as, for example, bis(benzonitrile) palladium(II) dichloride. This process may render the detection layer insoluble in organic solvents, and/or may enhance certain physical properties such as, for example, durability and/or abrasion resistance, which may be desirable for certain applications.

PIMs may be hydrophobic so that they will not absorb liquid water to an extent that the material swells significantly or otherwise exhibits a significant change in a physical property, although this is not a requirement. Such hydrophobic properties are useful in providing a sensor element that is relatively insensitive to the presence of water.

Detection layers may comprise a continuous matrix. Such a matrix is defined as an assembly (e.g., a coating and/or layer) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, or carbon nanotubes). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network. However, if such a latex or sol-gel layer can be consolidated such that individual particles are no longer discernible, nor is it possible to discern areas of the assembly that were obtained from different particles, such a layer may then be considered to be a continuous matrix.

In those embodiments wherein the measured physical parameter is capacitance or some other electrical property (including, but not limited to, capacitance, impedance, inductance, voltage, conductance, admittance, current, resistance, phase angle, loss factor, or dissipation) of the sensor element is detected, the detection layer should be a dielectric (i.e., it is non-conductive material). Changes in the dielectric constant (and optionally thickness) of the detection layer due to the presence of an adsorbed and/or absorbed organic compound within void spaces in the microporous material result in changes in the observed response of the sensor element with respect to the physical parameter.

Such measurable changes may be detected by an operating circuit that is in electrical communication with the first and second outer layers (which function in this embodiment as first and second respective electrodes). In this context, "operating circuit" refers generally to an electrical apparatus that can be used to apply a voltage to the first outer layer and the second outer layer (thus imparting a charge differential to the electrodes), and/or to monitor an electrical property of the sensor element, wherein the electrical property may change in response to the presence of an organic analyte. Examples of operating circuits include multimeters and computers.

Optionally, the first outer layer may be disposed on a base. The base should be selected such that it does not interfere with the function of the sensor element. The base may be conductive or non-conductive, depending on the sensor element configuration, for example, for sensor element designs in which the first outer layer is conductive, the base may be non-conductive (e.g., dielectric). Exemplary suitable bases include plastic films (e.g., polyester, polycarbonate, and polyolefin films), glass, and ceramic. In an exemplary process for making sensor elements useful in practice of the present disclosure, a dielectric base is provided (which may be a continuous slab, layer or film of material) that is in proximity to the first electrode and that may serve to provide physical strength and integrity to the finished sensor element. Any suitable material may be used, including, for example, glass, ceramic, and/or plastic. In large scale production, a polymeric film (such as polyester) may be used. In some embodiments, the dielectric base is an analyte-permeable material (e.g., silicone rubber or a microporous membrane).

In some embodiments, the first outer layer and the detection layer are in direct contact, with no interposing layer(s) therebetween. Likewise, in some embodiments, the second outer layer and the detection layer are in direct contact, with no interposing layer(s) therebetween. However, it is also contemplated that other, optional layers may be present between the first outer layer and the detection layer, and/or between the second outer layer and the detection layer. In such a case, at least a portion of one or both of the first and second outer layers may not be in direct contact with some or all of the detection layer. For example, a tie layer or layers may be used to improve the bonding between an electrode and the detection layer. Or, a passivation layer or layers (e.g., a layer of silicon dioxide) may be placed in between a surface of the detection layer and an electrode surface, in order to minimize the possibility of arcing between the electrodes. In some embodiments, multiple such optional layers may be used; alternatively a single layer may serve multiple functions. Any such optional layer or layers such, for example, as the aforementioned tie layers, passivation layers, protective layers, and cover layers may be used, for whatever purpose, as long as they do not significantly interfere with the desired functioning of the sensor element. For example, an optional layer should be sufficiently permeable by organic compounds of interest if the sensor element is configured such that the organic compound must pass through the optional layer in order to reach the detection layer.

In general, the edges of the first and/or second outer layers and/or detection layer can be aligned flush with each other, or, they may be recessed and/or extended relative to each other or any other layers that may be present.

During the deposition of the detection layer onto the first outer layer, an electrically accessible area may be provided on the first outer layer to enable electrical contact with an operating circuit. Similarly, if a cover layer is placed atop second outer layer, an electrically accessible area may be similarly provided. Such electrically accessible areas can be provided in any convenient location. In some embodiments, a connecting device (e.g., a contact pad, tab, or the like) may be placed in electrical contact with accessible area of first outer layer. Similarly, a connecting device may be placed likewise in contact with an accessible area of the second outer layer.

Improvement in performance of sensor elements can generally be achieved by heating the sensor element prior to exposure to an organic compound, for example, by heating the first outer layer (e.g., by resistive heating or using an external heating element), typically in combination with other components of the sensor element at a temperature of from 100° C. to 250° C. after deposition of the second outer layer. Soak times at these temperatures can have any duration, but typically fall in a range of minutes to hours.

In some embodiments, the first outer layer is provided on an optional substrate. The conductive layer may comprise any of the materials mentioned above, including blends or mixtures of conductive and nonconductive materials, and may be deposited by any suitable method, including but not limited to spin coating, dip coating, screen printing, transfer coating, sputter coating, physical vapor deposition, chemical vapor deposition, or a combination of two or more of such methods. In an alternate embodiment, the conductive layer may be provided by placing a premade film (e.g., a metal foil, conductive tape, etc.) atop the dielectric substrate. This first outer layer may be provided as a continuous layer or as a discontinuous layer, as previously described.

In some embodiments, the first outer layer is disposed in proximity to, and/or in contact with, at least a portion of the optional substrate. In an alternative embodiment, an optional layer may be present between at least a portion of the first outer layer, and the optional substrate. Such an optional layer may be used for any purpose (e.g., such as improving the bond between first outer layer and the substrate), as long as the layer does not interfere with the functioning of the sensor element.

For sensor element configurations designed to measure electrical properties (e.g., capacitance), conductive members (e.g., wire leads or traces) may be electrically coupled to the first and second outer layers at any appropriate point during assembly of the sensor element. For example, a first conductive member may be attached to the first outer layer immediately after deposition of the first outer layer and before deposition of the detection. In an alternative embodiment, the detection layer may be deposited on the first outer layer such that an area of the first outer layer is left exposed for attachment to a first conductive member. Similarly, a second conductive member may be attached to the second outer layer immediately after deposition of the second outer layer and before deposition of an optional cover layer, or the optional cover layer may be deposited on the second outer layer such that an area of the second outer layer is left exposed for attachment to the second conductive member.

In some embodiments, the microporous material is placed in proximity to the first outer layer by a coating process including, for example, solvent coating, spin coating, dip coating, transfer coating, and/or screen printing. In certain embodiments, the dielectric material is deposited in such a manner as to minimize the presence of defects, pinholes, etc. that might serve to compromise the performance of the sensor element. In a particular embodiment, the detection layer comprises a polymer of intrinsic microporosity (PIM) that is deposited by coating a solution comprising a PIM upon a suitable substrate and allowing the solution to dry so as to form a solid layer comprising the PIM material. Optionally, the construction may be heated to a temperature in a range of from 100° C. to 200° C. to further dry the coated material.

Detection layers can also be provided by other methods. For example, a preformed film of microporous material can be placed upon the first outer layer. In an alternative embodiment, the absorptive dielectric material can be provided in particulate form (e.g. as a powder, as a suspension, or as a sol) and deposited in such a form onto a first outer layer so as to form a particulate coating. If desired, such a material can be consolidated so as to form a continuous matrix of absorptive dielectric material.

Optional protective covers or barrier layers can be provided in proximity to the second outer layers. For example, in some embodiments, a cover layer can be placed atop the second outer layer, leaving an area of second outer layer accessible, for example, for electrical contact with a conductive member. Preferably, any such cover layer should not significantly interfere with the functioning of the sensor element. For example, if the sensor element is configured such that an analyte of interest must pass through cover layer in order to reach the detection layer, the cover layer should be sufficiently permeable by organic compounds of interest.

The optional cover layers may be deposited by any method known in the art, including coating (e.g. spin coating, dip coating, solvent coating, vapor coating, transfer coating, screen printing, flexographic printing, and the like). In an alternate embodiment, the cover layer can comprise a premade layer (e.g. a film or tape) that is placed upon the second outer layer. The optional cover layer may be provided such that the cover layer is in direct contact with at least a portion of a major surface of the second outer layer. The cover layer may be the outermost layer of the sensor element, or may itself receive additional coatings or layers if desired.

In some embodiments, adsorption/absorption of sufficient organic compound by at least one of the detection layers results in a detectable change in an electrical property associated with the sensor element (including but not limited to, capacitance, impedance, inductance, admittance, current, or resistance) may occur. Such a detectable change may be detected by an operating circuit that is in electrical communication with the first and second outer layers. In this context, "operating circuit" refers generally to an electrical apparatus that can be used to apply a voltage to the first outer layer and the second outer layer (thus imparting a charge differential to the electrodes), and/or to monitor an electrical property of the sensor element, wherein the electrical property may change in response to the presence of an organic analyte. Such an operating circuit may comprise a single apparatus which both applies voltage to the first and second outer layers, and monitors an electrical property. In an alternative embodiment, such an operating circuit may comprise two separate apparatuses, one to provide voltage, and one to monitor the signal. The operating circuit is typically electrically coupled to first outer layer and to second outer layer by conductive members.

Figure 3:
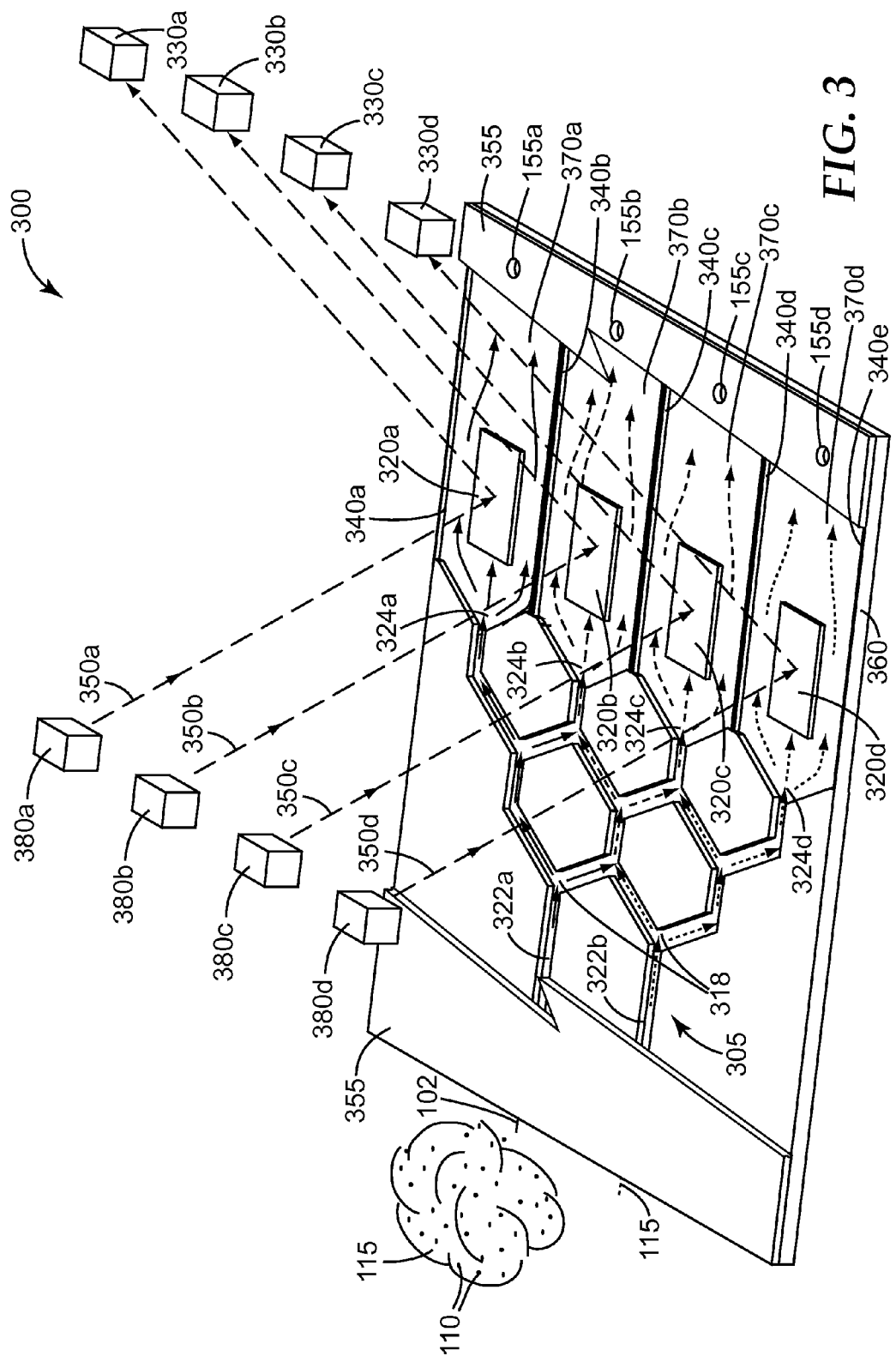
FIG. 3 is a cutaway schematic perspective view of an exemplary apparatus 300 suitable for practice of one embodiment of the present disclosure.
Figure 4A:
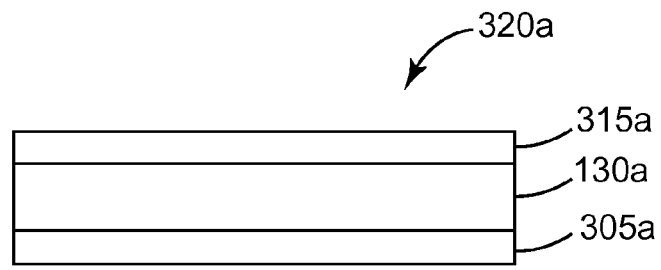
FIGS. 4A-4D are schematic views of respective sensor elements 320a, 320b, 320c, 320d in FIG. 3.
Figure 4B:
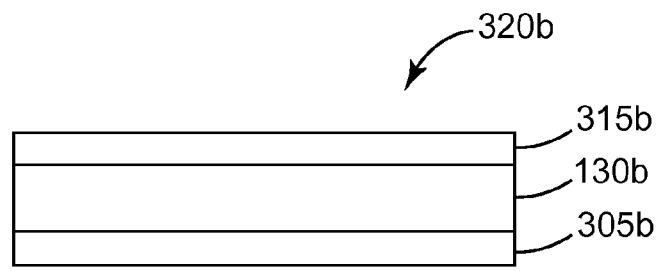
Figure 4C:
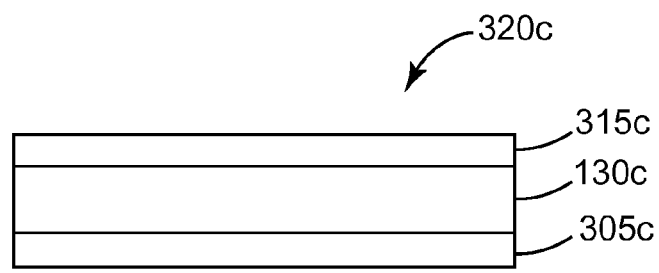
Figure 4D:
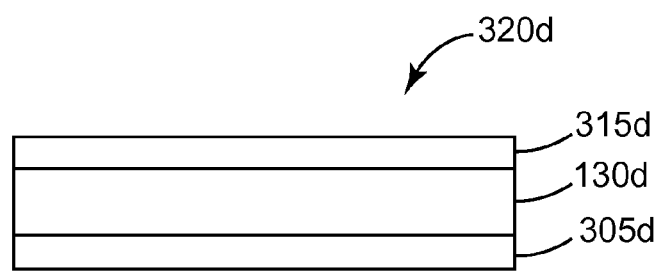

In FIGS. 1 and 3, gaseous medium 115 is combined with unknown organic compound 110 to form ambient sample 102.

In the embodiment shown in FIG. 1, sensor elements 120a, 120b, 120c, 120d are configured to detect electric properties (e.g., capacitance-based sensor elements). In this embodiment, each of respective first and second outer layers 125a, 135a, 125b, 135b, 125c, 135c, 125d, 135d of respective sensor elements 120a, 120b, 120c, 120d are conductive. Operating circuit 130 is in electrical communication via conductive members (132a, 132b, 134a, 134b, 136a, 136b, 138a, 138b) with sensor elements 120a, 120b, 120c, 120d. When connected to a source of electrical power, the operating circuit measures the capacitance (or other desired electrical property) of the sensor elements.

The operating circuit may be communicatively coupled to one or more of a data storage device, a computer processor, a process controller device, and/or a display device. In operation, the operating circuit is in electrical communication with a source of electrical power. Exemplary sources of electrical power include batteries, plug in power supplies, generators, hardwired power supplies, and radio frequency (RF) generators, if the operating circuit includes an RF receiver. Exemplary display devices include light emitting diode (LED) displays, liquid-crystal displays (LCDs), cathode ray tube (CRT) displays, galvanic meters, and printers. A controller device, if present, includes hardware and/or software that directs operation of the operating circuit. Exemplary data storage devices include flash memory devices, hard disks, digital tape, CD R media, and CD RW media.

In an alternative embodiment, the operating circuit may be provided in direct contact with the respective first and/or second outer layers, either via connecting members, or by contacting some portion of the operating circuit directly to an electrically accessible area of each electrode. For example, an operating circuit can be provided that resides on a circuit board or a flexible circuit (either of which can also serve as the dielectric substrate). The first outer layer can then be deposited directly onto the dielectric substrate such that it is in direct contact with a portion of the operating circuit.

Referring now to FIG. 3, exemplary optochemical sensor device 300 suitable for practicing the present disclosure includes dispenser channels 305 having an inlet openings 322a (to receive an ambient sample) and 322b (to receive a reference gas corresponding to the gaseous medium of the ambient sample) and a plurality of outlet openings 324a, 324b, 324c, 324d, which are independently in fluid communication with respective sensor elements 320a, 320b, 320c, 320d. Sensor elements 320a, 320b, 320c, 320d are configured to reflect light, and are disposed within respective isolated sensor chambers 370a, 370b, 370c, 370d, formed by walls 340a, 340b, 340c, 340d, 340e, base 360, and cover 355, such that they function independently. In this embodiment, the base and cover can comprise any solid material that is impermeable by the organic compound and gaseous media used, and do not collectively interfere with the ability of light to reflect from the sensor elements. Examples of useful materials include metal, glass, and plastic.

Sensor elements 320a, 320b, 320c, 320d are in fluid communication with respective outlet openings 324a, 324b, 324c, 324d of dispenser channels 305. Upon exposure of sensor elements 320a, 320b, 320c, 320d to an organic compound vapor, detection layers 130a, 130b, 130c, 130d will adsorb/absorb at least some of the unknown organic compound resulting in a change of refractive index and/or thickness of the sensor elements resulting in corresponding changes in the reflectance spectrum (e.g., optochemical sensor elements) of light that is incident on the second outer layers of the sensor elements.

Referring now to FIGS. 4A-4D, sensor elements 320a, 320b, 320c, 320d comprise respective at least partially reflective first outer layers 305a, 305b, 305c, 305d and respective semi-reflective second outer layers 315a, 315b, 315c, 315d. By the term "semi-reflective second outer layer" it is meant that each second outer layer reflects some incident light (e.g., at least 20, 30, 40, or 50 percent) and transmits (e.g., at least 20, 30, 40, or 50 percent) some incident light over a wavelength range of from 300 nanometers (nm) to 2500 nm, typically over a wavelength range of from 300 nm to 1100 nm. In this embodiment, the first outer layers are preferably highly (e.g., at least 50, 60, 70, 80, or even at least 90 percent) reflective. Although, the first outer layers are typically made to be more reflective (e.g., at least 50, 60, 70, 80, 90, 95, or even at least 99 percent reflective) than the semi-reflective second outer layer, in some embodiments, it may be desirable to have the reflectivity of the first and second outer layers be substantially the same. In other embodiments (not shown), the second outer layers can be made relatively highly reflective and the reflectivity of the first outer layers be reduced to make it semi-reflective; for example, so reflectance measurements can be made through the optional substrate.

In some embodiments, conductive ink, composed of silver or gold nanoparticles deposited at a thickness of 50 to 500 nm can be used to make outer layers (e.g., second outer layers) that are reflective, yet still permeable by the organic compound.

In the case of optochemical sensor elements, the first and second outer layers need not be conductive (e.g., as in the case of capacitance sensors). Accordingly, they may be made of any material having the desired reflective properties. Thickness of the first and second outer layers in this embodiment, will typically influence transparency (e.g., decreasing transparency with increasing thickness), and may adversely influence reflectivity if too thin (e.g., if less than one quarter of the wavelength of the incident radiation used).

Referring again to FIG. 3, light rays 350a, 350b, 350c, 350d from light sources 380a, 380b, 380c, 380d (e.g., tungsten filament bulbs, xenon lamps, light emitting diodes (LEDS), and/or at least one laser) incident on the sensor elements are reflected from both of the first and second outer layers of each sensor element resulting in interference effects that are manifested as changes in the respective spectrum of the reflected light (i.e., reflectance spectrum), which are detected via respective photodetectors 330a, 330b, 330c, 330d (e.g., spectrophotometers and/or photodiodes). It is also contemplated that a single light source may be used instead of multiple light sources.

Typically, the incident light includes one or more wavelengths in a range of from 300 nm to 2500 nm. The light emitted by the light source may be broad band (e.g., white light) or narrow band (e.g., LED or laser light). The characteristics of the light reflected from the sensor element result from the interference of light that is reflected from various layers (e.g., the reflective conductive electrode and the semi-reflective conductive electrode) and other interfaces of the sensor element. Such reflected light has a reflection spectrum with one or more spectral features (e.g., peaks, valleys, and/or inflection points) over a given wavelength range. The size and/or position of the spectral feature(s) changes in response to the presence of an analyte. Upon a shift in the position or size of one or more wavelength peaks (i.e., due to a change in the concentration of an analyte), the amount, spectral distribution, or intensity of reflected light that is detected by the photodetector may change.

Reflected light is analyzed using a photodetector capable of measuring reflection wavelength maximum band shifts. Reflection wavelength maximum band shifts can be readily obtained, for example, as wavelength shifts in reflection minima (valleys), maxima (peaks), or inflection points. As with capacitance, spectral changes are determined relative to a baseline reflection spectrum observed under identical conditions (e.g., temperature and humidity) in the absence of the analyte.

The photodetectors are communicatively coupled to one or more of a data storage device, a computer processor, a process controller device, and/or a display device (e.g., as discussed in reference to the embodiment shown in FIG. 3 above.

Further details concerning optochemical measurement techniques and apparatus are described in U.S. Pat. No. 7,556,774 (Rakow et al.) and U.S. Pat. No. 7,906,233 (Rakow et al.), U.S. Patent Appl. Publ. No. 2010/277740 A1 (Rakow et al.), and in U.S. Provisional Patent Appln. No. 61/475,000 entitled "METHOD OF DETECTING VOLATILE ORGANIC COMPOUNDS", filed Apr. 13, 2011, the disclosures of which are incorporated herein by reference.

Regardless of which of the foregoing sensor element configurations (e.g., capacitance or optochemical) is implemented, the second outer layers (and optionally the first outer layers) are preferably permeable by the unknown organic compound. Examples of porous conductive and/or semi-reflective second outer layers include, for example, thermal vapor deposited metallic films comprising metals such as copper, silicon, aluminum, rhodium, iridium, nickel, chromium, osmium, gold, silver, palladium, or a combination thereof. In principle, the second outer layer may have any thickness as long as it has sufficient conductivity and/or reflective characteristics (depending on the sensor design as discussed above), and as long as the first and/or second outer layers are sufficiently porous for the organic compounds in gaseous media to diffuse into the detection layer. Typically, these properties may be achieved at a thickness of from 1 nm to 50 nm, more typically from 1 nm to 10 nm, and even more typically from 4 nm to 8 nm, although other thickness may also be used. Greater thicknesses generally have undesirably low levels of permeability, while lesser thicknesses may become insufficiently conductive and/or difficult to electrically connect to the second conductive member. Desired thicknesses will typically depend on the material used to form the first outer layer, the material onto which the first and second outer layers are deposited, the organic compound to be detected, and the gaseous medium.

In exemplary embodiments, the second outer layers comprise at least one noble metal. In some embodiments, the second outer layer has a noble metal content of at least 50, 60, 70, 80, 90, 95, 99, or even at least 99.9 percent by weight. In some embodiments, the second outer layers consists of, or consists essentially of gold, palladium, platinum, or a combination thereof. The second outer layers may include additional components as long as it remains permeable by the organic compounds of interest. Combinations of different materials (conductive and/or nonconductive) can be used, as different layers or as a mixture, as long as sufficient overall conductivity and/or reflectivity and permeability is provided.

In some embodiments, the second outer layers can be prepared by a thermal vapor deposition process. In thermal vapor deposition, the material used to make the second electrode is heated under vacuum until it vaporizes and deposits on an appropriate component of the sensing element (e.g., the detection layer or an optional cover layer). Any suitable source of heating may be used; examples include resistive heating, laser heating, and e-beam heating (also termed e-beam evaporation). Thermal vapor deposition is generally carried out at pressures of about $10^{-5}$ torr (1 mPa), $10^{-6}$ torr (0.1 mPa), or lower. Thermal vapor deposition differs from sputter deposition. In sputter deposition, high energy atoms are bombarded into a target or source which then ejects material that deposits on a substrate. Typical pressures involved in sputter deposition are in the range of from $10^{-2}$ torr (1 Pa) to $10^{-4}$ torr (0.1 Pa), or higher.

In some embodiments, the first and/or second outer layers may also be etched or perforated to create holes or other open areas through which analyte can penetrate into the detection layer, although this is not a requirement. In such embodiments, the physical thickness of the detection layer may be in a range of from 150 nm to 1200 nm, for example, in a range of from 500 nm to 900 nm, although thinner and thicker detection layers may also be used.

Any number of sensor elements greater than one (e.g., greater than 2, greater than 3, greater than 4, greater than 5, greater than 10, or even greater than 20) may be used in practice of the present disclosure. First, second, third, etc. sensor elements may be operated independently (serially or in parallel) and may be located in separate devices.

Advantageously, sensor elements used in the present disclosure may be arranged within a single device and connected to a dispenser capable of supplying predetermined dilutions of the unknown organic compound based on (i.e., derived from) the ambient sample.

One such design is shown in FIG. 1, wherein dispenser channels 105 receives ambient sample 102 and divides it into two portions 104, 106. Portion 106 is passed through at least one porous filter 112 (e.g., an activated charcoal filter) that effectively removes the unknown organic compound (e.g., removes at least 95 percent, preferably at least 99 percent, and more preferably at least 99.99 percent of the unknown organic compound from the ambient sample) and optionally any water vapor that may be present, resulting in purified portion 107. Examples of suitable porous filters include activated carbon filters and porous dessicant filters. Portion 104 and purified portion 107 are then recombined through a branching network of flow channels 118 that are in fluid communication with outlet openings 124a, 124b, 124c, 124d.

It will be noted that while sensor element 120d shown in FIG. 1, which receives none of the organic material in the ambient sample, is not required for practice of the present disclosure, it may be useful, for example, for determining if porous filter 112 has reached the end of its useful life. Similarly, while sensor element 320d shown in FIG. 3, which receives none of the organic material in the ambient sample, is not required for practice of the present disclosure, it may be useful for determining if some experimental variable such as, for example, stray light has changed.

While dispenser channels 105 is shown in FIG. 1, it will be recognized that a configuration such as that shown in FIG. 3 and dispenser channels as 305 could also be used in its place.

Each of sensor elements 120a, 120b, and 120c receives a different concentration of the unknown compound, thereby allowing parallel measurement of various known dilutions of the ambient sample and reducing the time required for measurement. While the above design allows practice of the method without an external gas supply, it will be recognized that an external supply of a gas medium that is substantially equivalent to the second gaseous medium can also be used (e.g., as in the Examples hereinbelow).

Such a configuration is shown in FIG. 3, wherein dispenser channels 305 have a first inlet opening 322a, into which ambient sample 102 (as previously described) is introduced, and a second inlet opening 322b, into which the gaseous medium is introduced. As the ambient sample progresses through dispenser network of channels 318 to sensor chambers 370a, 370b, 370c, 370d and eventually leave the sensor device through openings 155a, 155b, 155c, 155d.

For use with environmental atmospheric samples, dry or humid air may be used as the gaseous medium. Effects of water vapor (humidity) on sensor response can typically be substantially eliminated by heating the sensor element at a temperature of at least about 50° C. (e.g., in a range of from 50° C. to 80° C., or at about 55° C.) while making sensor measurements of a specimen containing an organic compound. Other temperatures may also be used, for example, ambient temperature. In some embodiments, one or both of the first and second outer layers may be also be part of a heating element. The temperature of sensors may be controlled, for example, using flexible heaters and thermocouples using a feedback-loop controlling program.

Further details concerning sensor designs and methods for heating sensor elements can be found in U.S. Prov. Pat. Appl. No. 61/475,011, entitled "METHOD OF USING AN ABSORPTIVE SENSOR ELEMENT", filed Apr. 13, 2011, and U.S. Prov. Pat. Appl. No. 61/475,009, entitled "VAPOR SENSOR INCLUDING SENSOR ELEMENT WITH INTEGRAL HEATING", filed Apr. 13, 2011, the disclosures of which are incorporated herein by reference.

The ambient sample contains the unknown organic compound, which has an unknown chemical identity and is present at an unknown concentration, both of which can be determined according to the methods of the present disclosure.

Each of the sensor elements, whether a reference sensor element or not, exhibits a corresponding baseline response with respect to the presence of a gaseous medium in the absence of any organic compound at a specified temperature $T_o$. Preferably, the gaseous medium is selected such that it has little if any contribution to the response observed with the sensor element(s) (e.g., resulting in the same sensor element response as in a vacuum), although this is not a requirement. Similarly, each of the sensor elements, whether a reference sensor element or not, exhibits a corresponding observed response at $T_o$ with respect to the presence of the gaseous medium when it contains a positive level of the organic compound (e.g., known reference organic compound or unknown organic compound).

From the observed response and the baseline response for any given sensor element of the same basic design parameters, a normalized response can be calculated as the difference between the observed response and the baseline response, and that quantity divided by the baseline response. The general method for calculation of normalized response values is the same, whether in reference to a known reference organic compound or an unknown organic compound. Advantageously, using this normalization technique, the resultant values are generally insensitive to minor manufacturing tolerance variation in layer thicknesses between sensor elements (i.e., assuming no other changes in sensor element construction).

Figure 5:
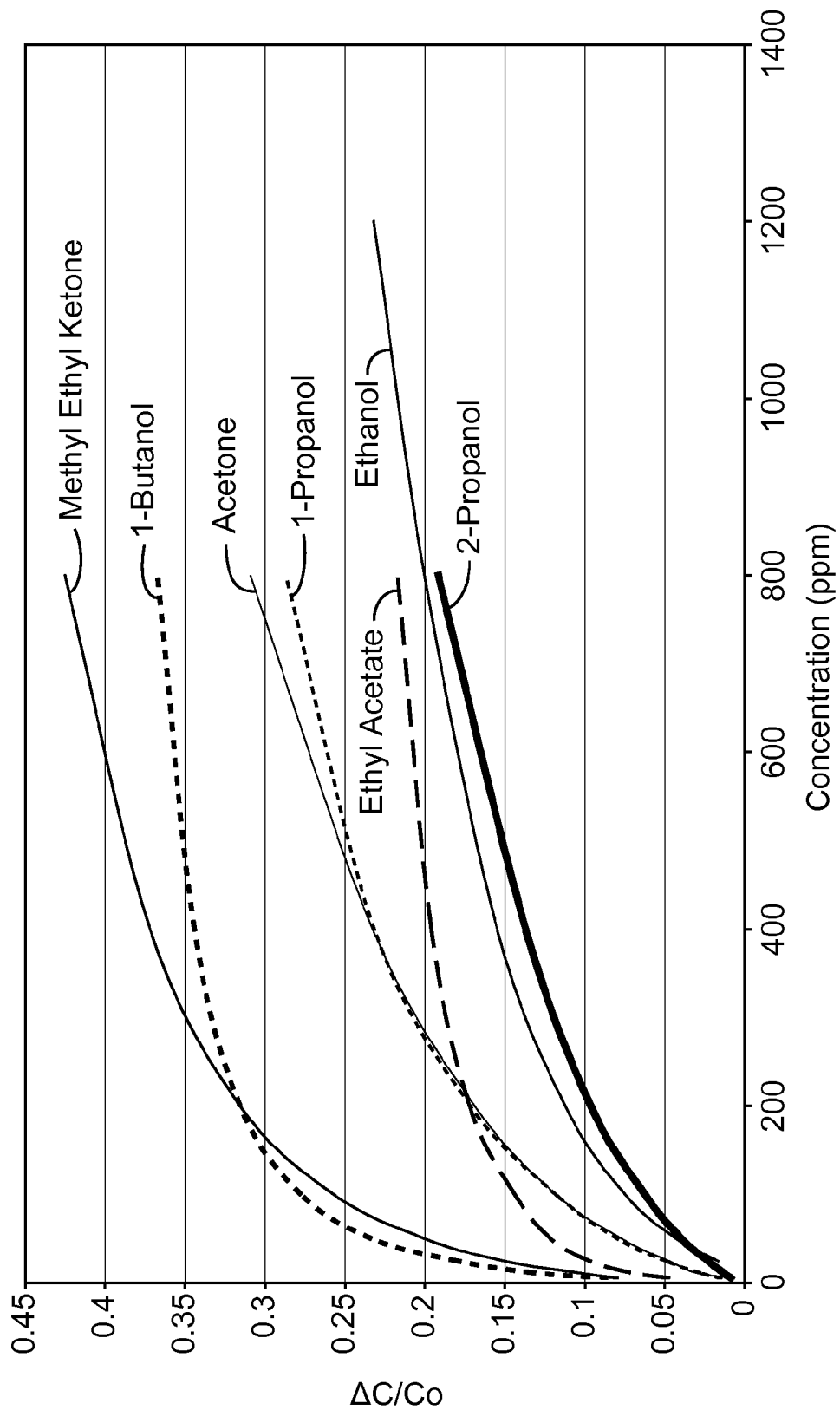
FIG. 5 is a graphical representation of the reference library used in Example 1.

The reference library comprises a plurality of reference normalized response correlations versus concentration of the respective organic compound in the gaseous medium or a substantial equivalent thereof. Each reference normalized response correlation corresponds to a different known reference organic compound having a respective different chemical identity with which the response of the sensor elements in the presence of the unknown organic compound can be compared. An exemplary reference library is shown in FIG. 5.

A set of such reference normalized response correlations each corresponding to a different known reference organic compound collectively comprise the reference library. While any known reference organic compounds may be included, it is preferable that organic compounds which are likely or expected for a given application are included in the reference library. The reference library may be obtained, for example, by careful measurement (e.g., using methods as described herein) of known reference compounds by a practitioner of one or more methods of the present disclosure, or the reference library may be obtained by another means. For example, the reference library may be supplied by a manufacturer of sensor elements used in practice of the present disclosure. Preferably, the reference library comprises reference normalized response correlations corresponding to at least 3, 5, 10, 15, or even at least 20 known reference organic compounds. Each reference normalized response correlation in the reference library is determined using a respective reference sensor element that is substantially identical to the first sensor element.

Depending on the dilution methodology used, and depending on whether a substantially equivalent (but not identical) diluent gas medium is used to prepare the various analytic and reference samples used in practice of the present disclosure, the composition of the second, third, fourth, fifth, sixth, etc. gaseous media may vary. As used herein, the term "substantially equivalent to" means not causing a substantial change in the response of the sensor element with respect to a physical parameter being measured. For consistency, the physical parameter of the sensor elements to be measured (e.g., capacitance or reflectance spectrum shift) is measured using substantially equivalent gaseous media at $T_o$ (e.g., the first, second, third, fourth, fifth, sixth, and seventh gaseous media are each substantially equivalent, and are preferably also equivalent to the first gaseous medium). Since the various gaseous media are selected such that they are substantially equivalent (and may be identical), there is essentially no effect of the gaseous media used on the resultant sensor response. Preferably, air, more preferably dry air, is used for at least one (or even all) of the gaseous media. Other gases that may be used alone or in combination with air or other gases as substantially equivalent gaseous media include non-organic diluent gases such as, for example, helium, argon, and nitrogen.

The ambient sample may be, for example, a continuous gaseous stream, an aliquot sample (e.g., supplied by syringe), or a series of aliquot samples (e.g., via an automatic gas sampler). The ambient sample may be representative of the atmosphere in a local environment, or it may be a derivative thereof (e.g., a dried version thereof), or is may be of some other specimen.

Once the analytic samples (e.g., first, second, and optional third analytic samples) have been contacted with the sensor element and the corresponding normalized responses determined for analytic samples containing the unknown organic compound, a normalized response correlation (e.g., which may be expressed as a mathematical relationship such as, for example, an equation or a graph) can be generated and compared to corresponding normalized response correlation for known organic compounds in a data set contained in the reference library.

Next, the reference normalized response correlation that most closely matches the normalized response correlation for the unknown organic compound is determined. Curve-fitting techniques (e.g., regression analysis such as, for example, least squares or weighted least squares analysis, and/or dynamic curve fitting techniques) may be advantageously used to aid in matching the unknown and reference normalized response correlations. In addition, matching the unknown and reference normalized response correlations may be advantageously accomplished using computer analysis software such as, for example, that available as EXCEL from Microsoft Corp., Redmond, Wash., or as SIGMAPLOT 12 from Systat Software Inc., San Jose, Calif.

In some cases, several possibilities may be present. In such cases, further discrimination may be accomplished by comparing the ratio of normalized responses (i.e., the reference normalized response divided by the unknown normalized response) against a known ratio of corresponding concentrations. For example, if the concentration decreases by a factor of 8, then the normalized response should likewise decrease by a factor of 8. Once matched to a reference normalized response correlation, the chemical identity of the organic material corresponding to that matched reference normalized response correlation is assigned to the unknown organic compound.

Knowing the chemical identity, it is a straightforward process to determine the concentration of the unknown organic compound from the observed normalized sensor element response of the ambient sample by determining that reference concentration $C^{ref}_m$ corresponding to a reference normalized response equal to $R^1_{norm}$. Concentration $C_1$ will be equal to concentration $C^{ref}_m$. Hence, knowing $C^{ref}_m$ and the ratio $C_{amb}/C_1$ (known from the dilution conditions chosen), $C_{amb}$ can be determined as $$C_{amb} = C^{ref}_m (C_{amb}/C_1).$$

In the above equation, it will be recognized that the ratio $C_{amb}/C_1$ corresponds to the dilution factor of the organic compound in the ambient sample, which is known. Hence, specific knowledge of neither $C_{amb}$ or $C_1$ is required to determine the ratio $C_{amb}/C_1$, and it is possible to use this equation to determine $C_{amb}$.

Accordingly, by following methods of the present disclosure, it is possible to readily determine (e.g., from a single sample) both the chemical identity and ambient concentration of an unknown organic compound (from among a set of known reference organic compounds).

Select Embodiments

In a first embodiment, the present disclosure provides a method of detecting an unknown organic compound in a first gaseous medium, the method comprising:

providing a first sensor element comprising a first outer layer, a second outer layer, and a detection layer comprising a microporous material disposed between the first outer layer and the second outer layer, wherein at least one of the first outer layer or the second outer layer is permeable by the unknown organic compound, wherein the unknown organic compound has an unknown chemical identity, wherein the first sensor element has a first baseline response ($R^1_o$) with respect to a physical parameter in a second gaseous medium at a fixed temperature ($T_o$), and wherein the second gaseous medium is substantially equivalent to the first gaseous medium;

providing a second sensor element, substantially identical to the first sensor element, wherein the second sensor element has a second baseline response ($R^2_o$) with respect to the physical parameter in the presence of the unknown organic compound in a third gaseous medium at $T_o$, wherein the third gaseous medium is substantially equivalent to the first gaseous medium;

providing a reference library comprising a plurality of reference normalized response correlations, wherein each reference normalized response correlation corresponds to a different known reference organic compound having a respective different chemical identity, wherein each reference normalized response correlation is determined using a respective reference sensor element that is substantially identical to the first sensor element, wherein each reference normalized response correlation correlates a respective variable concentration ($C^{ref}_{var}$) of a respective known reference organic compound with a respective quantity $$(R^{ref}_{var} - R^{ref}_o)/R^{ref}_o$$

wherein $R^{ref}_{var}$ is a response of the respective reference sensor element with respect to the physical parameter at the respective variable concentration $C^{ref}_{var}$ of the respective known reference organic compound in a respective fourth gaseous medium at $T_o$, wherein the fourth gaseous medium is substantially equivalent to the first gaseous medium, and wherein $R^{ref}_o$ for each respective reference sensor element corresponds to a baseline response in the fourth gaseous medium at $T_o$;

obtaining an ambient sample containing the first gaseous medium and the unknown organic compound, wherein the unknown organic compound is present in an ambient concentration ($C_{amb}$) in the ambient sample;

preparing a first analytic sample from the ambient sample, wherein the first analytic sample includes a first concentration ($C_1$) of the unknown organic compound in a fifth gaseous medium that is substantially equivalent to the first gaseous medium, wherein $C_1$ is known relative to $C_{amb}$;

preparing a second analytic sample from the ambient sample, wherein the second analytic sample includes a second concentration ($C_2$) of the unknown organic compound in a sixth gaseous medium that is substantially equivalent to the first gaseous medium, wherein $C_2$ is known relative to $C_{amb}$, wherein $C_1$ and $C_2$ are different, and wherein neither $C_1$ nor $C_2$ is zero;

exposing the first sensor element to the first analytic sample, measuring a first response ($R^1$) of the first sensor element with respect to the physical parameter at $T_o$, and obtaining a first normalized response $$R^1_{norm} = (R^1 - R^1_o)/R^1_o;$$

exposing the second sensor element to the second analytic sample, measuring a second response ($R^2$) of the second sensor element with respect to a physical parameter at $T_o$, and obtaining a second normalized response $$R^2_{norm} = (R^2 - R^2_o)/R^2_o; \text{ and}$$

comparing a data set comprising $R^1_{norm}$ at $C_1$ and $R^2_{norm}$ at $C_2$ to the plurality of reference normalized response correlations in the reference library;

selecting a matched normalized response correlation that best matches the data set from among the plurality of reference normalized response correlations in the reference library; and assigning the chemical identity of the known reference organic compound corresponding to the matched normalized response correlation to the unknown organic compound; and determining $C_{amb}$, by determining a reference concentration $C^{ref}_m$ associated with a normalized response value equal to $R^1_{norm}$ of the matched normalized response correlation, and then multiplying $C^{ref}_m$ by a known factor equal to $C_{amb}/C_1$.

In a third embodiment, the present disclosure provides a method according to the first or second embodiment, wherein the first gaseous medium comprises air.

In a fourth embodiment, the present disclosure provides a method according to any one of the first to third embodiments, wherein the first outer layer and the second outer layer are conductive, wherein the detection layer is dielectric, and wherein the physical parameter comprises capacitance of the first sensor element.

In a fifth embodiment, the present disclosure provides a method according to any one of the first to fourth embodiments, wherein the second outer layer is semi-reflective and the first outer layer is at least partially reflective, wherein the detection layer is optically transmissive, and wherein the physical parameter comprises a wavelength shift of reflected light that is incident on the first outer layer.

In a sixth embodiment, the present disclosure provides a method according to any one of the first to fifth embodiments, wherein the first analytic sample contains the same concentration of the unknown organic compound as the ambient sample.

In a seventh embodiment, the present disclosure provides a method according to any one of the first to sixth embodiments, wherein $T_o$ is in a range of from 40° C. to 80° C.

In an eighth embodiment, the present disclosure provides a method according to any one of the first to seventh embodiments, wherein the microporous material comprises an organic polymer of intrinsic microporosity.

In a ninth embodiment, the present disclosure provides a method according to the eighth embodiment, wherein the organic polymer of intrinsic microporosity comprises macromolecules comprising generally planar groups connected by rigid linkers, the rigid linkers having a point of contortion such that the generally planar groups adjacent to each of the rigid linkers are held in a non-coplanar orientation.

In a tenth embodiment, the present disclosure provides a method according to any one of the first to ninth embodiments, further comprising:

preparing a third analytic sample from the ambient sample, wherein the third analytic sample includes a third concentration ($C_3$) of the unknown organic compound in a seventh gaseous medium that is substantially equivalent to the first gaseous medium, wherein $C_3$ is known relative to $C_{amb}$, wherein the data set further comprises $R^3_{norm}$ at concentration $C_3$ of the unknown organic compound in the third analytic sample, wherein $R^3_{norm}$ is obtained by exposing a third sensor element to the third analytic sample, measuring a third response ($R^3$) of the third sensor element to the third analytic sample with respect to the physical parameter at $T_o$, and obtaining a third normalized response $R^3_{norm} = (R^3 - R^3_o)/R^3_o$, wherein the third sensor element is substantially identical to the first sensor element, wherein the third sensor element has a third baseline response ($R^3_o$) with respect to the physical parameter in the seventh gaseous medium at $T_o$, wherein $C_3$ is different than $C_1$ and $C_2$, and wherein $C_3$ is not zero.

In an eleventh embodiment, the present disclosure provides a method according to any of the first to tenth embodiments, wherein $C_{amb}$ and $C_1$ are the same.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Preparation of PIM Material

A PIM (Polymer of Intrinsic Microporosity) was prepared from the monomers 5,5',6,6'-tetrahydroxy-3,3,3',3'-tetramethyl-1,1'-spirobisindane and tetrafluoroterephthalonitrile generally according to the procedure reported by Budd et al. in Advanced Materials, 2004, Vol. 16, No. 5, pp. 456-459. 5,5',6,6'-tetrahydroxy-3,3,3',3'-tetramethyl-1,1'-spirobisindane (40.0 grams (g)) were combined with 23.7 g of tetrafluoroterephthalonitrile, 97.4 g potassium carbonate, and 1016.8 g of N,N-dimethylformamide, and the mixture was reacted at 68° C. for 72 hours. The polymerization mixture was poured into water, and the precipitate was isolated by vacuum filtration. The resulting polymer was twice dissolved in tetrahydrofuran, precipitated from ethanol, and air dried at room temperature. A yellow solid product was obtained having a number-average molecular weight of approximately 41,900 g/mole, as determined by gel permeation chromatography analysis using light scattering detection.

Method for Sensor Element Preparation

Sensor elements were prepared on PGO glass slides (glass number 0050-0050-0010-GF-CA, 50 mm×50 mm, 1.1 mm thick, material C-263, surface 80/50, obtained from Precision Glass & Optics, Santa Ana, Calif.), which were cleaned by soaking them in LIQUI-NOX detergent solution (obtained from Alconox, Inc., White Plains, N.Y.) for 30 to 60 minutes, then scrubbing each side of the slides with a bristle brush, rinsing them under warm tap water followed by a final rinse with deionized water (DI water). The slides were allowed to air dry covered to prevent dust accumulation on the surface. The dry, clean slides were stored in 3 in (7.6 cm) wafer carriers obtained from Entegris, Chaska, Minn.

A base conductive electrode was deposited onto the PGO glass slide by thermally vapor coating 10.0 nanometers (nm) of titanium (obtained as titanium slug, 9.5 mm×9.5 mm, 99.9+% purity from Alfa Aesar, Ward Hill, Mass.) at a rate of 0.1 nm per second (nm/sec) followed by thermal vapor coating 150.0 nm of aluminum (obtained as aluminum shot, 4-8 mm, PURATRONIC 99.999% from Alfa Aesar) at a rate of 0.5 nm/sec through a 2 in (5 cm)×2 in (5 cm) square mask (MASK A). MASK A had a single rectangular opening with a top border of 0.46 in (1.2 cm), a bottom border of 0.59 in (1.5 cm), and left and right borders of 0.14 in (0.35 cm) prepared from laser-cut 1.16 mm thick (24 gauge) stainless steel. The deposition process was controlled using an INFICON XTC/2 THIN FILM DEPOSITION CONTROLLER from INFICON of East Syracuse, N.Y.

A PIM solution of 5.5 percent by weight in chlorobenzene was prepared by mixing the components in a small jar and placing it on a roller mill (Mini Bottle Roller number 348920 from Wheaton Science Products, Millville, N.J.) for about 3 hours then filtering through an ACRODISC 25 MM SYRINGE FILTER WITH 1 MICRON GLASS FIBER MEMBRANE filter disk from PALL Life Sciences, Ann Arbor, Mich. The solution was allowed to sit overnight so that any bubbles that formed could escape.

Samples were spin-coated with the PIM solution using a Model WS 400B-8NPP/LITE spin coater from Laurell Technologies Corporation, North Wales, Pa. To coat a sample, it was placed in the spin coater and about 0.5 milliliter (mL) of chlorobenzene was placed on the sample. Each sample was spun for 15 seconds 300 rpm, then for 45 seconds at 2000 rpm. Then, one mL of the PIM solution was dispensed onto the sample and spin-coated at 300 rpm for 15 seconds and then at 2000 rpm for 45 seconds. After coating, the thickness of each PIM coating was measured using a Model XP-1 profilometer from AMBiOS Technology, Santa Cruz, Calif., by removing a small section of the coating with an acetone soaked cotton swab. The parameters used in the thickness measurement were a scan speed of 0.1 mm/sec, a scan length of 5 mm, a range of 10 micrometers, a stylus force of 0.20 mg and a filter level of 4. All of the samples were baked for 1 hour at 100° C. after coating. The average thickness of the PIM layers was 625 nm.

A top conductive electrode was deposited onto the PIM layer by thermally vapor coating 6 nm of gold (obtained as metal spatters, 99.999% typical purity from Cerac Inc., Milwaukee, Wis.) at a deposition rate of rate of 0.1 nm/sec through a 2 inch (5 cm)×2 inch (5 cm) mask (MASK B). MASK B had a 2×2 regular array of four 0.60 inch (1.5 cm) high×0.33 inch (0.84 cm) wide rectangular openings vertically separated by 0.22 inch (0.56 cm) and horizontally separated by 0.48 inch (1.2 cm) made from 24 gauge stainless steel by laser milling. The deposition process was controlled using an INFICON XTC/2 THIN FILM DEPOSITION CONTROLLER from Inficon, East Syracuse, N.Y.

After depositing the top conductive electrode, a connecting electrode (to facilitate electrical contact for testing) was deposited by thermally vapor coating 10.0 nm of titanium (obtained as titanium slug, 9.5 mm×9.5 mm, 99.9+% purity from Alfa Aesar) at a rate of 0.1 nm/sec followed by 150.0 nm of aluminum (obtained as aluminum shot, 4-8 mm, PURATRONIC 99.999% from Alfa Aesar) at a rate of 0.5 nm/sec through a 2 inch (5 cm)×2 inch (5 cm) mask (MASK C). MASK C had two horizontal rectangular openings with a height of 0.41 inch (1 cm), left and right borders of 0.14 inch (0.36 cm), and a separation of 0.92 inch (2.4 cm), prepared by laser milling from 24 gauge stainless steel. The deposition process was controlled using an INFICON XTC/2 THIN FILM DEPOSITION CONTROLLER.

This sensor element production process produced a set of four sensor elements of approximately 5 mm×6 mm active area (area under the overlapping semi-reflective conductive electrode and reflective conductive electrode that was not covered by the connecting electrode) on an approximately 50 mm×50 mm glass substrate. Individual sensor elements were produced by dicing the sample using a standard glass scoring cutter on the back (inactive side) while supporting the sensor elements so that the front (active) surfaces would not be damaged. After dicing, the sensor elements were tested for electrical shorts using a Protek multimeter, Model Number 6300, from Protek Test and Measurement, Norwood, N.J.

Capacitance Measurement Method

Before testing, the sensor elements were baked at 150° C. for 15 min in a convection oven.

The diluted vapor flowed into a detection device having four test chambers, each holding a sensor element coupled to a capacitance measurement system so that four separate samples could be measured at one time. The signal from the sensor was collected and the data was analyzed. Concurrently, the signal was also sent to an IR analyzer to verify the vapor concentrations.

All tests were performed in air that had been passed over DRIERITE desiccant (W. A. Hammond Drierite Co. Ltd., Xenia, Ohio) to remove moisture, and passed over activated carbon (Kuraray GG 12×29 obtained from Kuraray Chemical Co., Ltd., Osaka, Japan) to eliminate any organic contaminates.

An apparatus was assembled that had a sealed dilution/detection system set up to deliver a vapor to a test chamber. Various vapor levels (concentrations) were generated using a KD Scientific syringe pump (available from KD Scientific Inc., Holliston, Mass.) fitted with a 500-microliter gas tight syringe (obtained from Hamilton Company, Reno, Nev.). The syringe pump delivered an organic liquid onto a 42.5 mm diameter disk of filter paper (#1 Qualitative Filter Paper available from the Whatman division of GE Healthcare, Fairfield, Conn.) suspended in the middle neck of a 500-mL three-necked flask. Dry air was introduced at a flow rate of 10 liters/minute (L/min) into the flask in another neck, and the air flow past the filter paper vaporized the solvent (VOC) and carried it out of the third neck to a set of flow meters that served as the dilution system. Delivering the solvent at different rates by controlling the syringe pump generated different concentrations of vapor. The syringe pump was controlled by a LABVIEW program (software available from National Instruments, Austin, Tex.) was used to generate vapor profiles during each test. A set of flow meters (Omega Engineering, Inc., Stamford, Conn.) was used to fractionate the vapor stream into four streams. The first stream was undiluted and flowed into the first test chamber at 5 L/min; 50 percent of the stream flowed into the second test chamber, 25 percent of the stream flowed into the third test chamber, and 12.5 percent of the stream flowed into the fourth test chamber. A stream of dry air was fractionated into test chambers 2, 3, and 4 so that the flow rate through each chamber was 5 L/min to produce three dilutions.

In each test chamber, the capacitance and dissipation factors were measured with an LCR meter (Instek Model 821 LCR Meter from Instek America Corp., Chino, Calif.) applying one volt at 1000 Hz across the top and base electrodes. The capacitance data were collected and stored using the same LABVIEW program that controlled the syringe pump and temperature.

Concurrently, a MIRAN IR analyzer (available from Thermo Fischer Scientific, Inc. of Waltham, Mass.) was used to verify the set concentrations.

The experiments were conducted at ambient temperature (approximately 21° C.).

Example 1

Generation of a Reference Library of Reference Normalized Response Curves

A reference library containing reference normalized capacitance (i.e., response) correlations, was generated according to the procedure described in the CAPACITANCE MEASUREMENT METHOD (described hereinabove) at ambient temperature using various volatile organic compounds (VOCs). The reference normalized capacitance correlations were in the form of $\Delta C/C_o$=(measured capacitance ($C_{meas}$) minus the baseline capacitance ($C_o$))/$C_o$=($C_{meas}$−$C_o$)/$C_o$ measured at known VOC vapor concentrations. $C_o$ is the capacitance of the sensor in the absence of the organic compound under otherwise the same conditions. Reference normalized capacitance correlations were generated for seven volatile organic compounds (VOCs). In the examples below, dry air was used as the gaseous medium and the temperature was 21° C. Results are reported in Table 2, and shown graphically in FIG. 5. The VOCs used were:

1. Acetone—obtained as OMNISOLV ACETONE (stock number AX0116-6) from EMD Chemicals Inc., Gibbstown, N.J.
2. MEK (Methyl Ethyl Ketone)—stock number 9319-01, obtained from J. T. Baker, Phillipsburg, N.J.
3. Ethyl Acetate—obtained as OMNISOLV ETHYL ACETATE (stock number EX0241-6) from EMD Chemicals Inc.
4. 2-Propanol—obtained as OMNISOLV 2-Propanol (stock number PX1835-6) from EMD Chemicals Inc.
5. Ethanol—Cat #111000200, obtained from PHARMCO-AAPER, Brookfield, Conn.
6. 1-Propanol—stock number 9086-01, obtained from J. T. Baker 7. 1-Butanol—obtained as OMNISOLV 1-BUTANOL (stock number BX1777-6) from EMD Chemicals Inc.

Sensor measurements were made at a dry air/VOC flow rate of 5 liters/minute (L/min) with no dilution going into the test chamber. Reference normalized capacitance correlations were generated for the reference VOCs, using the normalized capacitances at various concentrations reported in Table 2 (below), which are graphically represented in FIG. 5.

TABLE 2

| CONCENTRATION, parts per million (ppm) | NORMALIZED CAPACITANCE ($\Delta C/C_o$) | | | | | | |
|---|---|---|---|---|---|---|---|
| | acetone | MEK | ethyl acetate | 2-propanol | ethanol | 1-propanol | 1-butanol |
| 6 | 0.0069 | 0.0798 | 0.0468 | 0.0090 | | 0.0150 | 0.0854 |
| 12 | 0.0307 | 0.1043 | 0.0712 | 0.0135 | | 0.0283 | 0.1325 |
| 25 | 0.0473 | 0.1505 | 0.0970 | 0.0229 | 0.0168 | 0.0493 | 0.1795 |
| 50 | 0.0769 | 0.2001 | 0.1214 | 0.0394 | 0.0428 | 0.0797 | 0.2332 |
| 100 | 0.1180 | 0.2568 | 0.1438 | 0.0624 | 0.0748 | 0.1180 | 0.2774 |
| 200 | 0.1689 | 0.3156 | 0.1721 | 0.0964 | 0.1123 | 0.1717 | 0.3156 |
| 400 | 0.2328 | 0.3719 | 0.1961 | 0.1371 | 0.1549 | 0.2319 | 0.3443 |
| 800 | 0.3093 | 0.4253 | 0.2171 | 0.1917 | 0.2004 | 0.2869 | 0.3674 |
| 1200 | | | | | 0.2321 | | |

Identification of Unknown VOCs

From the seven VOCs in Table 2, each corresponding to a VOC represented in the reference library prepared above, four were arbitrarily selected to be used as "unknown" organic compounds. Each of the "unknown" VOC analytic samples was fractionated, and dilutions (i.e., analytic samples) were prepared by mixing together fractions of the "unknown" VOC analytic samples with dry air at a dilution factor of 2, 4, and 8, as reported in Table 3 (below).

TABLE 3

| Dilution Ratio | undiluted | 1:1 | 1:3 | 1:7 |
|---|---|---|---|---|
| Dilution Factor | 1 | 2 | 4 | 8 |
| percent of original "unknown" VOC concentration | 100 | 50 | 25 | 12.5 |
| Vapor Output Flow Rate, liters/minute | | | | |
| Dry air with "unknown" VOC | 5.0 | 2.500 | 1.250 | 0.625 |
| Dry air | 0 | 2.500 | 3.750 | 4.375 |

The "unknown" VOC analytic samples were tested as in the case of the reference organic compounds (above) at the original concentration and at each dilution, at ambient temperature. While four "unknown" VOC analytic samples were tested, only dilution factors 1 and 8 for each VOC analytic sample were used in the determination of the "unknown" VOC analytic samples. The four "unknown" VOC analytic samples were A (200 ppm of methyl ethyl ketone), B (400 ppm of ethyl acetate), C (500 ppm of acetone) and D (200 ppm of 2-propanol). The "unknown" VOC analytic samples were tested using the dilution/detection system used to generate the reference library, with monitoring the change in capacitance ($\Delta C$) for each sample at the 100 percent and 12.5 percent of original concentration levels (corresponding to dilution factors 1 and 8). All of the capacitance measurements were converted into $\Delta C/C_o$ (normalized capacitance) to make them comparable with the reference normalized capacitance correlations in the reference library.

Identification and Quantification of "Unknown" VOC Analytic Samples

Figure 6:
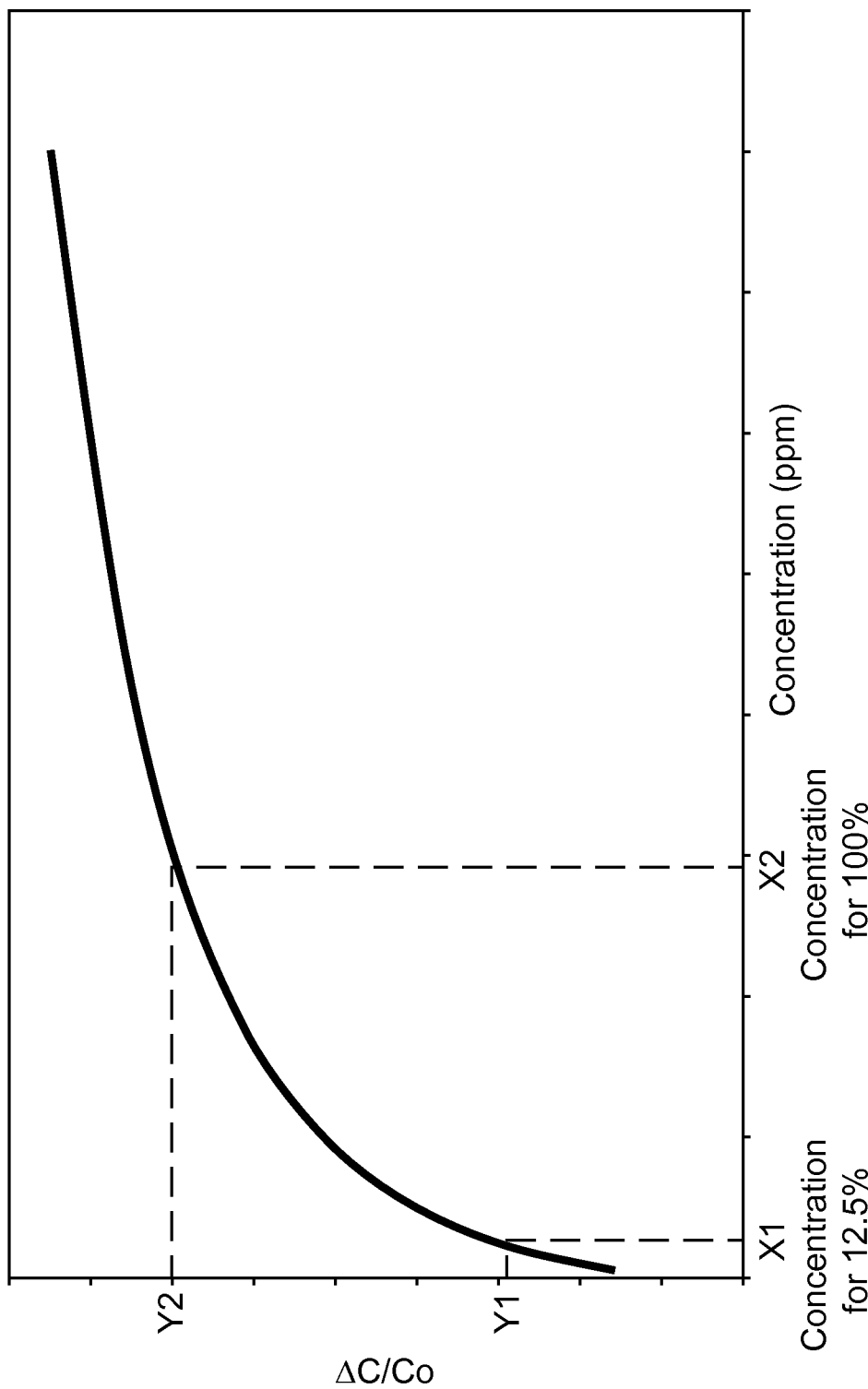
FIG. 6 is an exemplary vapor response curve for an unknown organic compound in Example 1.

The observed normalized capacitance curves in the reference library (FIG. 5) were then graphically compared with the $\Delta C/C_o$ data for the "unknown" analytic samples (e.g., as shown in FIG. 6). Table 4 shows measurement data obtained for all four "unknown" VOCs and the seven reference VOCs in the reference library. The data is represented as an equivalent concentration (ppm) for each $\Delta C/Co$ value of the specific unknown solvent. In 15 out of 28 correlations between the "unknown" samples, the reference library made a positive match that indicated possible identity of the unknown VOC. The other measurements (N/A) did not match any of the reference curves. However, this step by itself was not sufficient to identify any of the "unknown" samples. For example, the "unknown" VOC analytic sample A could have been one of two possible vapors MEK and 1-butanol. For the "unknown" VOC analytic sample B, only 2-propanol and ethanol were eliminated as potential identities of the VOC in the "unknown" VOC analytic sample.

TABLE 4

| "UNKNOWN" VOC SAMPLE | $\Delta C/C_o$ AT CONCENTRATION X2, $\Delta C/C_o$ AT CONCENTRATION X1 | CONCENTRATION CORRESPONDING TO NORMALIZED CAPACITANCE VALUES IN REFERENCE LIBRARY, ppm | | | | | | |
|---|---|---|---|---|---|---|---|---|
| | | acetone | MEK | ethyl acetate | 2-propanol | ethanol | 1-propanol | 1-butanol |
| A | 0.316, | N/A, | 197.0, | N/A, | N/A, | N/A, | N/A, | 197.5, |
| | 0.145 | 146.5 | 23.5 | 97.7 | 452.5 | 859.0 | 143.4 | 14.6 |
| B | 0.197, | 275.0, | 47.4, | 412.4, | N/A, | N/A, | 270.8, | 31.5, |
| | 0.121 | 103.0 | 15.8 | 50.0 | 303.0 | 656.8 | 103.0 | 9.9 |
| C | 0.259, | 527.2, | 103.3, | N/A, | N/A, | N/A, | 595.2, | 73.3, |
| | 0.092 | 65.8 | 9.2 | 21.7 | 183.5 | 449.5 | 64.4 | 6.9 |
| D | 0.098, | 73.0, | 10.5, | 25.9, | 207.5, | 491.9, | 71.5, | 7.5, |
| | 0.024 | 9.0 | N/A | 3.1 | 26.0 | 82.0 | N/A | N/A |

In Table 4, N/A indicates that the value obtained for the unknown was so far from the solvent curve that it could be eliminated as a possibility for the identity of the unknown. In Table 4, Concentration X2 corresponds to 100 percent of the VOC concentration (i.e., high concentration) in the "unknown" VOC analytic sample, and Concentration X1 corresponds to 12.5 percent of the VOC concentration (i.e., low concentration) in the "unknown" VOC analytic sample (see FIG. 6).

To identify the "unknown" VOC analytic samples, an additional step was performed utilizing the dilution ratio information of the measured analyte. The original vapor streams were diluted to 12.5 percent of their original concentration so that the dilution factor was eight. The ratio between a pair of concentrations for an "unknown" VOC (one measured at 100 percent and one at 12.5 percent) for this example should also be 8. Hence, the "unknown" VOC analytic sample having a ratio value closest to 8 corresponded to the predicted identity of "unknown" VOC analytic sample. Table 5 summarizes the high/low concentration ratios of all of the possibilities for the identity of each "unknown" from Table 4. In Table 5, an X indicates that the normalized response values were too different to correspond to the actual VOC. Based on their closeness to 8, the predicted identities of A, B, C, and D are reported in the italics in Table 5 (below).

TABLE 5

| UNKNOWN VOC | NORMALIZED CAPACITANCE AT HIGH CONCENTRATION/ NORMALIZED CAPACITANCE AT LOW CONCENTRATION | | | | | | |
|---|---|---|---|---|---|---|---|
| ANALYTIC SAMPLE | acetone | MEK | ethyl acetate | 2-propanol | ethanol | 1-propanol | 1-butanol |
| A | X | 8.38 | X | X | X | X | 13.53 |
| B | 2.67 | 3.00 | 8.25 | X | X | 2.63 | 3.18 |
| C | 8.01 | 11.23 | X | X | X | 9.24 | 10.62 |
| D | 8.11 | X | 8.30 | 7.98 | 6.00 | X | X |

Table 6 summarizes the predicted identities of the four "unknown" samples used in this example, and how they compared to the actual solvents and concentrations that were used. Predicted VOC concentrations in Table 6 (below) were determined by reference to the normalized capacitance correlations in the reference library (e.g., see FIG. 5).

TABLE 6

| UNKNOWN | ACTUAL SOLVENT USED | ACTUAL CONCEN- TRATION, ppm | PREDICTED SOLVENT | PREDICTED CONCEN- TRATION, ppm | PERCENT ERROR IN CONCEN- TRATION |
|---|---|---|---|---|---|
| A | MEK | 200 | MEK | 197 | −1.5 |
| B | ethyl acetate | 400 | ethyl acetate | 412.4 | 3.1 |
| C | acetone | 500 | acetone | 527.2 | 5.44 |
| D | 2-propanol | 200 | 2-propanol | 207.5 | 3.75 |

As can be seen in Table 6, the above method for qualitative and quantitative detection of VOCs correctly indentified all four "unknown" VOC analytic samples, and estimated their concentrations with relatively small error.

All patents and publications referred to herein are hereby incorporated by reference in their entirety. All examples given herein are to be considered non-limiting unless otherwise indicated. Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A method of detecting an unknown organic compound in a first gaseous medium, the method comprising:

providing a first sensor element comprising a first outer layer, a second outer layer, and a detection layer comprising a microporous material disposed between the first outer layer and the second outer layer, wherein at least one of the first outer layer or the second outer layer is permeable by the unknown organic compound, wherein the unknown organic compound has an unknown chemical identity, wherein the first sensor element has a first baseline response ($R^1_o$) with respect to a physical parameter in a second gaseous medium at a fixed temperature ($T_o$), and wherein the second gaseous medium is substantially equivalent to the first gaseous medium;

providing a second sensor element, substantially identical to the first sensor element, wherein the second sensor element has a second baseline response ($R^2_o$) with respect to the physical parameter in the presence of the unknown organic compound in a third gaseous medium at $T_o$, wherein the third gaseous medium is substantially equivalent to the first gaseous medium;

providing a reference library comprising a plurality of reference normalized response correlations, wherein each reference normalized response correlation corresponds to a different known reference organic compound having a respective different chemical identity, wherein each reference normalized response correlation is determined using a respective reference sensor element that is substantially identical to the first sensor element, wherein each reference normalized response correlation correlates a respective variable concentration ($C^{ref}_{var}$) of a respective known reference organic compound with a respective quantity $(R^{ref}_{var} - R^{ref}_o)/R^{ref}_o$ wherein $R^{ref}_{var}$ is a response of the respective reference sensor element with respect to the physical parameter at the respective variable concentration $C^{ref}_{var}$ of the respective known reference organic compound in a respective fourth gaseous medium at $T_o$, wherein the fourth gaseous medium is substantially equivalent to the first gaseous medium, and wherein $R^{ref}_o$ for each respective reference sensor element corresponds to a baseline response in the fourth gaseous medium at $T_o$;

obtaining an ambient sample containing the first gaseous medium and the unknown organic compound, wherein the unknown organic compound is present in an ambient concentration ($C_{amb}$) in the ambient sample;

preparing a first analytic sample from the ambient sample, wherein the first analytic sample includes a first concentration ($C_1$) of the unknown organic compound in a fifth gaseous medium that is substantially equivalent to the first gaseous medium, wherein $C_1$ is known relative to $C_{amb}$;

preparing a second analytic sample from the ambient sample, wherein the second analytic sample includes a second concentration ($C_2$) of the unknown organic compound in a sixth gaseous medium that is substantially equivalent to the first gaseous medium, wherein $C_2$ is known relative to $C_{amb}$, wherein $C_1$ and $C_2$ are different, and wherein neither $C_1$ nor $C_2$ is zero;

exposing the first sensor element to the first analytic sample, measuring a first response ($R^1$) of the first sensor element with respect to the physical parameter at $T_o$, and obtaining a first normalized response $$R^1_{norm}=(R^1-R^1_o)/R^1_o;$$

exposing the second sensor element to the second analytic sample, measuring a second response ($R^2$) of the second sensor element with respect to a physical parameter at $T_o$, and obtaining a second normalized response $$R^2_{norm}=(R^2-R^2_o)/R^2_o;\text{ and}$$

comparing a data set comprising $R^1_{norm}$ at $C_1$ and $R^2_{norm}$ at $C_2$ to the plurality of reference normalized response correlations in the reference library;

selecting a matched normalized response correlation that best matches the data set from among the plurality of reference normalized response correlations in the reference library;

assigning the chemical identity of the known reference organic compound corresponding to the matched normalized response correlation to the unknown organic compound; and determining $C_{amb}$, by determining a reference concentration $C^{ref}_m$ associated with a normalized response value equal to $R^1_{norm}$ of the matched normalized response correlation, and then multiplying $C^{ref}_m$ by a known factor equal to $C_{amb}/C_1$.

2. The method of claim 1, wherein the first outer layer is disposed on a substrate.

3. The method of claim 1, wherein the first gaseous medium comprises air.

4. The method of claim 1, wherein the first outer layer and the second outer layer are conductive, wherein the detection layer is dielectric, and wherein the physical parameter comprises capacitance of the first sensor element.

5. The method of claim 1, wherein the second outer layer is semi-reflective and the first outer layer is at least partially reflective, wherein the detection layer is optically transmissive, and wherein the physical parameter comprises a wavelength shift of reflected light that is incident on the first outer layer.

6. The method of claim 1, wherein the first analytic sample contains the same concentration of the unknown organic compound as the ambient sample.

7. The method of claim 1, wherein $T_o$ is in a range of from 40° C. to 80° C.

8. The method of claim 1, wherein the microporous material comprises an organic polymer of intrinsic microporosity.

9. The method of claim 8, wherein the organic polymer of intrinsic microporosity comprises macromolecules comprising generally planar groups connected by rigid linkers, the rigid linkers having a point of contortion such that the generally planar groups adjacent to each of the rigid linkers are held in a non-coplanar orientation.

10. The method of claim 1, further comprising:

preparing a third analytic sample from the ambient sample, wherein the third analytic sample includes a third concentration ($C_3$) of the unknown organic compound in a seventh gaseous medium that is substantially equivalent to the first gaseous medium, wherein $C_3$ is known relative to $C_{amb}$, wherein the data set further comprises $R^3_{norm}$ at concentration $C_3$ of the unknown organic compound in the third analytic sample, wherein $R^3_{norm}$ is obtained by exposing a third sensor element to the third analytic sample, measuring a third response ($R^3$) of the third sensor element to the third analytic sample with respect to the physical parameter at $T_o$, and obtaining a third normalized response $R^3_{norm}=(R^3-R^3_o)/R^3_o$, wherein the third sensor element is substantially identical to the first sensor element, wherein the third sensor element has a third baseline response ($R^3_o$) with respect to the physical parameter in the seventh gaseous medium at $T_o$, wherein $C_3$ is different than $C_1$ and $C_2$, and wherein $C_3$ is not zero.

11. The method of claim 1, wherein $C_{amb}$ and $C_1$ are the same.

* * * * *